United States Patent
Nivorozhkin et al.

(10) Patent No.: US 7,135,491 B2
(45) Date of Patent: *Nov. 14, 2006

(54) 5-ARYLTETRAZOLE COMPOUNDS AND USES THEREOF

(75) Inventors: Alex Nivorozhkin, West Roxbury, MA (US); John Van Duzer, Georgetown, MA (US); Andrew Salzman, Belmont, MA (US); Garry Southan, Lynn, MA (US); Siya Ram, Winchester, MA (US); Qi Zeng, North Andover, MA (US); Csaba Szabo, Gloucester, MA (US)

(73) Assignee: Inotek Pharmaceuticals Corp., Beverly, MA (US)

( * ) Notice: Subject to any disclaimer, the term of this patent is extended or adjusted under 35 U.S.C. 154(b) by 84 days.

This patent is subject to a terminal disclaimer.

(21) Appl. No.: 11/030,536

(22) Filed: Jan. 6, 2005

(65) Prior Publication Data

US 2005/0159467 A1 Jul. 21, 2005

Related U.S. Application Data

(60) Division of application No. 10/620,619, filed on Jul. 17, 2003, which is a continuation-in-part of application No. 10/197,609, filed on Jul. 18, 2002.

(51) Int. Cl.
A61K 31/41 (2006.01)
(52) U.S. Cl. ..................................................... 514/381
(58) Field of Classification Search .................. 514/381
See application file for complete search history.

(56) References Cited

U.S. PATENT DOCUMENTS

| | | | |
|---|---|---|---|
| 5,049,572 | A | 9/1991 | Scherrer et al. |
| 5,232,937 | A | 8/1993 | Makovec et al. |
| 5,284,954 | A | 2/1994 | Wittenberger |
| 5,364,869 | A | 11/1994 | De et al. |
| 5,663,357 | A | 9/1997 | Teng et al. |
| 5,874,593 | A | 2/1999 | Ushio |
| 5,976,576 | A | 11/1999 | Makovec et al. |
| 6,191,136 | B1 | 2/2001 | Marban |
| 6,191,289 | B1 | 2/2001 | Ushio |
| 6,277,998 | B1 | 8/2001 | Ushio |
| 6,281,222 | B1 | 8/2001 | Salzman et al. |
| 6,297,261 | B1 | 10/2001 | Christopherson et al. |
| 6,388,088 | B1 | 5/2002 | Sidduri |
| 6,417,393 | B1 | 7/2002 | Christopherson et al. |
| 6,569,862 | B1 | 5/2003 | Marban |
| 6,696,479 | B1 | 2/2004 | Van Der Schaaf et al. |
| 6,706,749 | B1 | 3/2004 | Dahl et al. |
| 2002/0032210 | A1 | 3/2002 | Dahl et al. |
| 2002/0037905 | A1 | 3/2002 | Dahl et al. |
| 2002/0103202 | A1 | 8/2002 | Pinto et al. |
| 2003/0186998 | A1 | 10/2003 | Marban |
| 2003/0229120 | A1 | 12/2003 | Olsen et al. |
| 2004/0019208 | A1 | 1/2004 | Nivorozhkin et al. |

FOREIGN PATENT DOCUMENTS

| | | |
|---|---|---|
| EP | 0638553 | 7/1994 |
| JP | 10025294 | 1/1998 |
| WO | WO 90/09989 | 9/1990 |
| WO | WO 93/16053 | 8/1993 |
| WO | WO 98/58522 | 12/1998 |
| WO | WO 99/24038 | 5/1999 |
| WO | WO 99/24442 | 5/1999 |
| WO | WO 00/16798 | 3/2000 |
| WO | WO 00/24707 | 5/2000 |
| WO | WO 00/28979 | 5/2000 |
| WO | WO 00/64888 | 11/2000 |
| WO | WO 01/66098 | 9/2001 |
| WO | WO 01/85705 | 11/2001 |
| WO | WO 02/00647 | 1/2002 |

OTHER PUBLICATIONS

Oda et al., Oxygen radicals in influenza-induced pathogenesis and treatment with pyran polymer-conjugated SOD, Science. May 26, 1989;244(4907):974-6.
Tan et al. ,Xanthine oxidase activity in the circulation of rats following hemorrhagic shock, Free Radic Biol Med. Oct. 1993; 15(4):407-14.
McCord J.M., Oxygen-derived free radicals in postischemic tissue injury, N Engl J Med. Jan. 17, 1985;312(3):159-63
Miesel et al., "Effects of allopurinol on in vivo suppression of arthritis in mice and ex vivo modulation of phagocytic production of oxygen radicals in whole human blood",Inflammation. Dec. 1994;18(6):597-612.
Engerson et al., Conversion of xanthine dehydrogenase to oxidase in ischemic rat tissues,J Clin Invest. Jun. 1987;79(6):1564-70.
Akaide et al., Dependance on O2- generation by xanthine oxidase of pathogenesis of influenza virus infection in mice,J Clin Invest. Mar. 1990;85(3):739-45.
Ketai et al., Plasma hypoxanthine and exercise. *Am Rev Respir Dis.* Jul. 1987; 136(1):98-101.
Mohacsi et al., Neutrophils obtained from obliterative atherosclerotic patients exhibit enhanced resting respiratory burst and increased degranulation in respose to various stimuli, Biochim Biophys Acta. Aug. 23, 1996;1316(3):210-6.
Friedl et al. Ischemia-reperfusion in humans. Apperance of xanthine oxidase activity. Am J Pathol. Mar. 1990;136(3):491-5.
Friedl et al., Roles of histamine, complement and xanthine oxidase in thermal injury of skin.Am J Pathol. Jul. 1989;135(1):203-17.
Parks et al., Role of oxygen free radicals in shock, ischemia, and organ preservation.Surgery. Sep. 1983;94(3):428-32.

(Continued)

Primary Examiner—Taofiq Solola
(74) Attorney, Agent, or Firm—Wilmer Cutler Pickering Hale and Dorr LLP

(57) ABSTRACT

The present invention relates to 5-Aryltetrazole Compounds, compositions comprising an effective amount of a a 5-Aryltetrazole Compound, and methods for treating an inflammation disease, a reperfusion disease, or hyperuricemia in an animal in need thereof comprising administering to the animal an effective amount of a 5-Aryltetrazole compound.

13 Claims, No Drawings

OTHER PUBLICATIONS

Demling et al., Lung oxidant changes after zymosan peritonitis: relationship between physiologic and biochemical changes.Am Rev Respir Dis. Nov. 1992;146(5 Pt 1):1272-8.

Chambers et al., Xanthine oxidase as a source of free radical damage in myocardial ischemia. J Mol Cell Cardiol. Feb. 1985;17(2):145-52.

Deitch et al., Hemorrhagic shock-induced bacterial translocation is reduced by xanthine oxidase inhibition or inactivation.Surgery. Aug. 1988;104(2):191-8.

Mayumi et al., Zonal heterogeneity of hepatic injury following shock/resuscitation: relationship of xanthine oxidase activity to localization of neutrophil accumulation and central lobular necrosis. Shock. May 1996;5(5):324-32.

Flynn et al., Allopurinol plus strandard resuscitation preserves hepatic blood flow and function following hemorrhagic shock.J Trauma. Dec. 1994;37(6):956-61.

Zollei, I., Experimental study of hypovolaemic shock-induced gastric mucosal lesions in the rat. Ann Acad Med Singapore. Jan. 1999;28(1):85-9.

Modelska et al., Inhibition of beta-adrenergic-dependent alveolar epithelial clearance by oxidant mechanisms after hemorrhagic shock. Am J. Physiol. May 1999;276(5 Pt 1):L844-57.

Flynn et al., Xanthine oxidase inhibition prevents mesenteric blood flow deficits after resuscitated hemorrhagic shock by preserving endothelial function. J Surg Res. Mar. 1997;68(2):175-80.

Mannion et al., Role of xanthine oxidase inhibition in survival from hemorrhagic shock. Circ Shock. Jan. 1994;42(1):39-43.

Cunningham and Keaveny, Effect of a xanthine oxidase inhibitor on adenine nucleotide degradation in hemorrhagic shock. Eur Surg Res. 1978;10(5):305-13.

Youn et al., Oxidants and the pathophysiology of burn and smoke inhalation injury. Free Radic Biol Med. 1992;12(5):409-15.

Deitch et al., A study of the relationship among survival, gut-origin sepsis, and bacterial translocation in a model of systemic inflammation.J Trauma. Feb. 1992;32(2):141-7.

Anderson et al., Hypovolemic shock promotes neutrophil sequestration in lungs by a xanthine oxidase-related mechanism. J Appl Physiol. Nov. 1991;71(5):1862-5.

Pogetti et al., Simultaneous liver and lung injury following gut ischemia is mediated by xanthine oxidase. J Trauma. Jun. 1992;32(6):723-7; discussion 727-8.

Nielsen et al., Xanthine oxidase inactivation attenuates postocclusion shock after descending thoracic aorta occlusion and reperfusion in rabbits. J Thorac Cardiovasc Surg. Sep. 1995;110(3):715-22.

Schwartz et al., Xanthine oxidase-derived oxygen radicals increase lung cytokine expression in mice subjected to hemorrhagic shock. Am J Respir Cell Mol Biol. Apr. 1995;12(4):434-40.

Crowell et al., Effect of allopurinol on hemorrhagic shock. Am J Physiol. Apr. 1969;216(4):744-8.

Linder et al., Cellular expression of xanthine oxidoreductase protein in normal human tissues. Lab Invest. Aug. 1999;79(8):967-74.

Saksela et al., Xanthine oxidoreductase gene expression and enzyme activity in developing human tissues. Biol Neonate. Oct. 1998;74(4):274-80.

Battelli et al., Determination of xanthine oxidase in human serum by a competitive enzyme-linked mmunosorbent assay (ELISA). Clin Chim Acta. Mar. 1999;281(1-2):147-58.

Houston et al., Binding of xanthine oxidase to vascular endothelium. Kinetic characterization and oxidative impairment of nitric oxide-dependent signaling. J Biol Chem. Feb. 19, 1999;274(8):4985-94.

Fox et al., Immunohistochemical localization of xanthine oxidase in human retina. Free Radic Biol Med. Apr. 1998;24(6):900-5.

Rouquette et al., Xanthine oxidoreductase is asymmetrically localised on the outer surface of human endothelial and epithelial cells in culture. FEBS Lett. Apr. 24, 1998;426(3):397-401.

Cardillo et al., Xanthine oxidase inhibition with oxypurinol improves endothelial vasodilator function in hypercholesterolemic but not in hypertensive patients. Hypertension. Jul. 1997;30(1 Pt 1):57-63.

Page et al., Xanthine oxidoreductase in human mammary epithelial cells: activation in response to inflammatory cytokines. Biochim Biophys Acta. Jul. 23, 1998;1381(2):191-202.

Zhang et al., Generation of nitric oxide by a nitrite reductase activity of xanthine oxidase: a potential pathway for nitric oxide formation in the absence of nitric oxide synthase activity. Biochem Biophys Res Commun. Aug. 28, 1998;249(3):767-72

Trujillo et al., Xanthine oxidase-mediated decomposition of S-nitrosothils. J Biol Chem. Apr. 3, 1998;273(14):7828-34.

Goldfinger, S.E., Treatment of gout. N Engl J Med. Dec. 2, 1971;285(23):1303-6.

Buchanan et al., Hypocholesterolemic 5-substituted tetrazoles. J Med Chem. Nov. 1969;12(6):1001-6.

Shukla and Rastogi, Studies on neuropharmacological and biochemical properties of 5- substituted tetrazoles. Indian J Physiol Pharmacol. Oct.-Dec. 1981;25(4):369-73.

Springer et al., 1916, J. Med. Chem. 19, 291: U.S. Appl. No.: 4,021,556.

Skipper et al., Inhibition of experimental neoplasms by 4-aminopyrazolo (3,4-d) pyrimidine. Proc Soc Exp Biol Med. Aug. 1955;89(4):594-6.

Demko and Sharpless, Preparation of 5-substituted 1H-tetrazoles from nitriles in water. J Org Chem. Nov. 30, 2001;66(24):7945-50.

Butler, R.N., Comprehensive Heterocyclic Chemistry, Katritsky, et al., Eds., Pergamon: Oxoford, U.K., 1996 vol. 4.

Isida et al. , The Formation of Tin-Nitrogen Bonds. V. The Selective 1-Substitution Reaction of 5-Substituted 1-(Tri-n-butylstannyl tetrazoles) with Methyl Iodide,Methyl p- Toluenesulfonate, Dimethyl Sulfate, and Ethyl Bromoacetate. Chemical Society of Japan, vol. 46, 2176-2180.(1973).

Rosenbaum et al., 1992 "Thermolyse von 1-Thiocarbamoyl-5-phenyl-tetrazolen", J. Prakt. Chem. 334:283-4.

Myznikov et al., Tetrazoles XXV. Production of N-benzoyltetrazoles and their chemical characteristics. J. Org. Chem. USSR Dec. 20, 1988 24(7):1397-1401.

A. Konnecke et al., 1976, Tetrahedron letters, No. 7, 533-536.

Oshipova et al., Tetrazoles XIX. Acylation of tetrazoles under the conditions of phase- transfer catlysis. J. Org. Chem. USSR 1984 20(11):2248-2252.

Jursic B.S., 1993, "Acyltetrazole As an Intermediate for Preparation of Carboxylic Acid Derivatives", Synthetic Communications, 23(3):361-4.

Ichibuchi et al., Synthesis and structure-activity relationships of 1-phenylpyrazoles as xanthine oxidase inhibitors. *Bioorg. Med. Chem. Lett.* 2001 11(7):879-882.

Nagamatsu et al., Novel xanthine oxidase inhibitor studies. Part 2. Synthesis and xanthine oxidase inhibitory activities of 2-substituted 6-alkyl-indenehydrazino- or 6- arylmethylijndenenehydrazino-7H-purines and 3- and/or 5-substituted 9H-1,2,4- triazoleo[3,4-i]purines. *J. Chem. Soc. Perkin Trans. 1* 1999 3117-3125.

Baldwin et al. , 1975, 4-Trifluoromethylimidazoles and 5-(4-Pyridyl)-1,24-triazoles, New Classes of Xanthine Oxidase Inhibitors: J. Of Med. Chemistry, v. 18 No. 9.

J. of Org. Chem of the USSR, Russian Original vol. 20., No. 5, Part 2, May 1984.

Czuczwar et al., A potential anti-asthmatic drug, CR 2039, enhances the anticonvulsive activity of some antiepileptic drugs against pentetrazol in mice. Eur Neuropsychopharmacol. Aug. 1998;8(3):233-8.

Czuzwar et al., Influence of a potential anti-asthmatic drug, CR 2039, upon the anticonvulsive activity of conventional antiepileptics against maximal electroshock- induced seizures in mice. J Neural Transm. 1996;103(12):137-9.

Makovec F., Antiallergic and cytoprotective activity of new N-phenylbenzamido acid derivatives. J Med Chem. Oct. 2, 1992;35(20):3633-40.

Revel et al. ,CR 2039, a new bis-(1H-tetrazol-5-yl)phenylbenzamide derivative with potential for the topical treatment of asthma. Eur J Pharmacol. Dec. 8, 1992;229(1):45-53.

Revel et al., Pharmacological profile of CR 2039 (Dizolast) a new agent for the treatment of allergic diseases, Life Sciences, 229:273-7. 1992.

Persiani et al., Pharmacokinetics of andolast after administration of single escalating doses by inhalation in mild asthmatic patients. Biopharm Drug Dispos. Mar. 2001;22(2):73-81.

Blake et al., 1997, "Xanthine Oxidase: Four Roles for the Enzyme in Rheumatoid Pathology" Biochemical Society Transactions, 25:1-7.

Boros et al., 1989, "Oxygen Free Radical-Induced Histamine Release During Intestinal Ischemia and Reperfusion", Eur. Surg. Res. 21:297-304.

Brown et al., 1988, "Xanthine Oxidase Produces Hydrogen Peroxide which Contributes to Reperfusion Injury of Ischemic, Isolated, Perfused Rat Hearts", J. Clin. Invest. 81:1297-301.

Deliconstantinos et al., 1996, "Alterations of Nitric Oxide Synthase and Xanthine Oxidase Activities of Human Keratinocytes by Ultraviolet B Radiation", Biochem. Pharm. 51:1727-1738.

Harrison, R., 1997, "Human Xanthine oxidoreductase: In Search of a Function", Biochemical Society Transactions 25: 1-7.

Vorbach et al., The housekeeping gene xanthine oxidoreductase is necessary for milk fat droplet enveloping and secretion: gene sharing in the lactating mammary gland. *Genes Dev.* Dec. 15, 2002;16(24):3223-35.

5-ARYLTETRAZOLE COMPOUNDS AND USES THEREOF

This application is a division of U.S. application Ser. No. 10/620,619. filed Jul. 17, 2003, which is a continuation-in-part of U.S. application Ser. No. 10/197,609, filed Jul. 18, 2002, which is currently pending, the entirety of each being incorporated herein by reference.

GOVERNMENTAL SUPPORT

The research leading to the invention was supported, at least in part, by a grant from: the National Institute of General Medical Sciences Grant No. 1R43 GM63274-01A1; the National Heart, Lung, and Blood Institute Grant No. 1R43HL70342-01; the National Institute of General Medical Sciences Grant No. 2R44GM59017-02; and the National Institute of General Medical Sciences Grant No. 1R43GM59017-01. Accordingly, the U.S. Government may have certain rights in the invention.

1. FIELD OF THE INVENTION

The present invention relates to 5-Aryltetrazole Compounds, compositions comprising an effective amount of a 5-Aryltetrazole Compound, and methods for treating or preventing an inflammation disease, a reperfusion disease, or hyperuricemia comprising administering to an animal in need thereof an effective amount of a 5-Aryltetrazole Compound.

2. BACKGROUND OF THE INVENTION

The level of xanthine oxidase ("XO") in an animal increases markedly (>400-fold in bronchoalveolar fluid in pneumonitis) during inflammation, ischemia-reperfusion injury, and atherosclerosis. Particularly, due to the spillover of tissue XO into the circulation, plasma levels of XO may be detected in an animal experiencing adult respiratory distress syndrome, ischemia-reperfusion injury, arthritis, sepsis, hemorrhagic shock, and other inflammatory conditions. Inflammation-induced histamine release by mast cells and basophils also enhances the activity of XO.

Superoxide radical ($O_2^-$) can be generated by xanthine oxidase and NADPH oxidase from the partial reduction of molecular oxygen. Neutrophils and macrophages are known to produce $O_2^-$ and hydrogen peroxide ($H_2O_2$), which normally are involved in the killing of ingested or invading microbes (T. Oda et al., *Science*, 244:974–976). Under physiologic conditions XO is ubiquitously present in the form of a xanthine dehydrogenase (XDH). XDH is a molybdenum iron-sulfur flavin dehydrogenase that uses $NAD^+$ as an electron acceptor to oxidize purines, pyrimidines, pteridins, and other heterocyclic nitrogen-containing compounds. In mammals, XDH is converted from the NAD-dependent dehydrogenase form to the oxygen-dependent oxidase form, either by reversible sulfhydryl oxidation or irreversible proteolytic modification (S. Tan et al., *Free Radic. Biol. Med.* 15:407–414). Xanthine oxidase then no longer uses $NAD^+$ as an electron acceptor, but transfers electrons onto oxygen, generating $O^{2-}$, $H_2O_2$, and hydroxyl radical (OH) as purines are degraded to uric acid (J. M. McCord et al., *New Engl. J. Med.* 312:159–163; R. Miesel et al., *Inflammation*, 18:597–612). Inflammatory activation converts XDH to XO, mainly by oxidizing structurally important thiolates. Inflammation also markedly up-regulates the conversion of xanthine dehydrogenase (T. D. Engerson et al., *J. Clin. Invest.* 79:1564–1570).

Inhibition of XO activity blocks the formation of $O_2^-$ and prevents loss of purine nucleotides, and is therefore salutary in a variety of shock and ischemia reperfusion disorders. Pharmacologic inhibition of XO can also be beneficial by blocking the pro-inflammatory effect of $O_2^-$ on gene expression (M. D. Schwartz et al., *Am. J. Respir. Cell. Mol. Biol.*, 12:434–440). $O_2^-$ has been implicated in the nuclear translocation of NF-kappa B and the expression of NF-icB-dependent genes. In mice subjected to hemorrhagic shock, depletion of XO by a tungsten-enriched diet decreased mononuclear mRNA levels of IL-113 and TNF-a. Similar results were obtained after pharmacologic inhibition of XO by in vivo administration of allopurinol. A vicious cycle can be created by oxidant stress, in which $O_2^-$ induction of pro-inflammatory cytokines results in greater XDH to XO conversion, and thus more $O_2^-$ production. This suggests that XO inhibitors can exert important anti-inflammatory actions by interrupting this process at multiple points, in particular, by blocking pro-inflammatory gene expression.

Pharmacologic inhibition of XO can also be beneficial in hemorrhagic shock by preserving the intracellular nucleotide pool. Under conditions of energetic failure, induced by hypoxia or by oxidant-induced poly(ADP-ribose) synthetase activation, high energy phosphate nucleotides are sequentially degraded to inosine monophosphate, xanthine, and hypoxanthine. In the presence of XO and molecular oxygen, xanthine and hypoxanthine degrade to uric acid, thereby depleting the purine pool. The loss of available purines with which to form ATP accelerates the loss of intracellular energetics and contributes to cell necrosis and organ failure. XO inhibitors block this terminal degradative pathway and permit the cell to recover and reestablish adequate stores of high energy phosphate nucleotides. In a canine model of severe hemorrhagic shock, pre-treatment with allopurinol resulted in a 6-fold increase in survival (J. W. Crowell et al., *Am. J. Phys.* 216:744–748). When the administration of allopurinol was delayed until after shock had been produced, allopurinol exerted no benefit. Infusion of the purine base hypoxanthine after the onset of shock similarly provided no benefit. When allopurinol and hypoxanthine were co-infused, however, there was a dramatic increase in survival (no survival in control group at 16 hours post-shock vs. a 40% survival in the treated group at 48 hours). Similar results were obtained in a canine model of hemorrhagic shock in which allopurinol significantly improved survival, whereas a cocktail of free-radical scavengers (superoxide dismutase, catalase, dimethylsulfoxide, and alpha tocopherol) had no effect (D. Mannion, et al., *Circ. Shock,* 42:39–43). Thus, XO blockade appears to be beneficial by three independent mechanisms: blockade of $O_2^-$ formation; inhibition of $O_2^-$ mediated pro-inflammatory gene expression; and preservation of the nucleotide pool available for ATP formation.

Accordingly, there is a clear need for compounds that inhibit the levels of xanthine oxidase in an animal and, accordingly, that are useful for treating or preventing an inflammation disease, a reperfusion disease, or hyperuricemia.

Citation of any reference in Section 2 of this application is not an admission that the reference is prior art to the application.

3. SUMMARY OF THE INVENTION

The invention encompasses compounds having the formula (Ia):

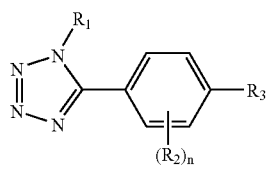

and pharmaceutically acceptable salts and hydrates thereof, wherein:

$R_1$ is $CO_2R_4$;

each $R_2$ is independently -halo, —$NO_2$, —CN, —OH, —$N(R_5)(R_5)$, —$OR_5$, —$C(O)R_5$, —$OC(O)R_5$, —$C(O)NHC(O)R_5$, —$(C_1$–$C_{10})$alkyl, —$(C_2$–$C_{10})$alkenyl, —$(C_2$–$C_{10})$alkynyl, —$(C_3$–$C_{10})$cycloalkyl, —$(C_8$–$C_{14})$bicycloalkyl, —$(C_5$–$C_{10})$cycloalkenyl, —$(C_3$–$C_{10})$heterocycle, -phenyl, -naphthyl, -benzyl, —$CO_2R_5$, —$C(O)OCH(R_5)(R_5)$, —$NHC(O)R_5$, —$NHC(O)NHR_5$, —$C(O)NHR_5$, —$OC(O)R_5$, —$OC(O)OR_5$, —$SR_5$, —$S(O)R_5$, or —$S(O)_2R_5$;

$R_3$ is —H, -halo, —$NO_2$, —CN, —OH, —$N(R_5)(R_5)$, —$O(CH_2)_mR_5$, —$C(O)R_5$, —$C(O)N(R_5)(R_5)$, —$C(O)NH(CH_2)_m(R_5)$, —$OCF_3$, -benzyl, —$CO_2CH(R_5)(R_5)$, —$(C_1$–$C_{10})$alkyl, —$(C_2$–$C_{10})$alkenyl, —$(C_2$–$C_{10})$alkynyl, —$(C_3$–$C_{10})$cycloalkyl, —$(C_8$–$C_{14})$bicycloalkyl, —$(C_5$–$C_{10})$cycloalkenyl, -naphthyl, —$(C_3$–$C_{10})$heterocycle, —$CO_2(CH_2)_mR_5$, —$NHC(O)R_5$, —$N(R_5)C(O)R_5$, —$NHC(O)NHR_5$, —$OC(O)(CH_2)_mCHR_5R_5$, —$CO_2(CH_2)_mCHR_5R_5$, —$OC(O)OR_5$, —$SR_5$, —$S(O)R_5$, —$S(O)_2R_5$, —$S(O)_2NHR_5$, or

$R_4$ is —$(C_5)$heteroaryl, —$(C_6)$heteroaryl, phenyl, naphthyl, or benzyl;

each $R_5$ is independently —H, —$CF_3$, —$(C_1$–$C_{10})$alkyl, -benzyl, -adamantyl, -morpholinyl, -pyrrolidyl, -pyrridyloxide, -pyrrolidinyldione, -piperdidyl, —$(C_2$–$C_{10})$alkenyl, —$(C_2$–$C_{10})$alkynyl, —$(C_3$–$C_{10})$cycloalkyl, —$(C_8$–$C_{14})$bicycloalkyl, —$(C_3$–$C_{10})$heterocycle, or

each $R_6$ is independently —H, -halo, —$NO_2$, —CN, —OH, —$CO_2H$, —$N((C_1$–$C_{10})$alkyl$(C_1$–$C_{10})$alkyl), —$O(C_1$–$C_{10})$alkyl, —$C(O)(C_1$–$C_{10})$alkyl, —$C(O)NH(CH_2)_m(C_1$–$C_{10})$alkyl, —$OCF_3$, -benzyl, —$CO_2(CH_2)_mCH((C_1$–$C_{10})$alkyl$(C_1$–$C_{10})$alkyl), —$C(O)H$, —$CO_2(C_1$–$C_{10})$alkyl, —$(C_1$–$C_{10})$alkyl, —$(C_2$–$C_{10})$alkenyl, —$(C_2$–$C_{10})$alkynyl, —$(C_3$–$C_{10})$cycloalkyl, —$(C_8$–$C_{14})$bicycloalkyl, —$(C_5$–$C_{10})$cycloalkenyl, —$(C_5)$heteroaryl, —$(C_6)$heteroaryl, -phenyl, naphthyl, —$(C_3$–$C_{10})$heterocycle, —$CO_2(CH_2)_m(C_1$–$C_{10})$alkyl, —$CO_2(CH_2)_mH$, —$NHC(O)(C_1$–$C_{10})$alkyl, —$NHC(O)NH(C_1$–$C_{10})$alkyl, —$OC(O)(C_1$–$C_{10})$alkyl, —$OC(O)O(C_1$–$C_{10})$alkyl, —$SO_2NHR_5$, or —$SO_2NH_2$;

n is an integer ranging from 0 to 4;

each m is independently an integer ranging from 0 to 8; and each p is independently an integer ranging from 0 to 5.

A compound of formula (Ia) or a pharmaceutically acceptable salt or hydrate thereof is useful for treating or preventing an inflammation disease, a reperfusion disease, or hyperuricemia in an animal.

The invention also relates to pharmaceutical compositions comprising an effective amount of a compound of formula (Ia) or a pharmaceutically acceptable salt or hydrate thereof; and a pharmaceutically acceptable carrier or vehicle. These compositions are useful for treating or preventing an inflammation disease, a reperfusion disease, or hyperuricemia in an animal.

The invention also relates to compounds of formula (Ib):

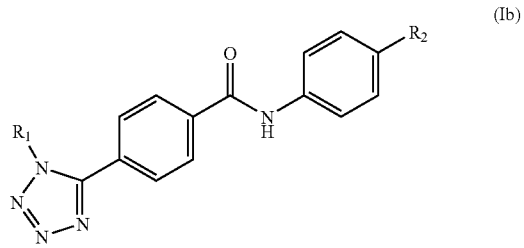

and pharmaceutically acceptable salts and hydrates thereof, wherein:

$R_1$ is —H, —$CO_2R_4$, —$C(O)R_5$, or —$C(O)N(R_5)(R_5)$;

$R_2$ is —$(C_1$–$C_{10})$alkyl or —$O(C_1$–$C_{10})$alkyl;

$R_4$ is —$(C_5)$heteroaryl, —$(C_6)$heteroaryl, phenyl, naphthyl, or benzyl; and each $R_5$ is independently —H, —$CF_3$, —$(C_1$–$C_{10})$alkyl, -benzyl, —$(C_2$–$C_{10})$alkenyl, —$(C_2$–$C_{10})$alkynyl, —$(C_3$–$C_{10})$cycloalkyl, —$(C_8$–$C_{14})$bicycloalkyl, —$(C_3$–$C_{10})$heterocycle.

A compound of formula (Ib) or a pharmaceutically acceptable salt or hydrate thereof is useful for treating or preventing an inflammation disease, a reperfusion disease, or hyperuricemia in an animal.

The invention also relates to pharmaceutical compositions comprising an effective amount of a compound of formula (Ib) or a pharmaceutically acceptable salt or hydrate thereof; and a pharmaceutically acceptable carrier or vehicle. These compositions are useful for treating or preventing an inflammation disease, a reperfusion disease, or hyperuricemia in an animal.

The invention further relates to methods for treating or preventing an inflammation disease, comprising administering to an animal in need thereof an effective amount of a compound of formula (Ia) or (Ib) or a pharmaceutically acceptable salt or hydrate thereof.

The invention further relates to methods for treating or preventing a reperfusion disease, comprising administering to an animal in need thereof an effective amount of a compound of formula (Ia) or (Ib) or a pharmaceutically acceptable salt or hydrate thereof.

The invention further relates to methods for treating or preventing hyperuricemia, comprising administering to an animal in need thereof an effective amount of a compound of formula (Ia) or (Ib) or a pharmaceutically acceptable salt or hydrate thereof.

The invention further relates to methods for treating or preventing tumor-lysis syndrome, comprising administering to an animal in need thereof an effective amount of a compound of formula (Ia) or (Ib) or a pharmaceutically acceptable salt or hydrate thereof.

The invention further relates to methods for treating or preventing an inflammatory bowel disorder, comprising administering to an animal in need thereof an effective amount of a compound of formula (Ia) or (Ib) or a pharmaceutically acceptable salt or hydrate thereof.

The invention further relates to methods for inhibiting xanthine oxidase activity, comprising administering to an animal in need thereof an effective amount of a compound of formula (Ia) or (Ib) or a pharmaceutically acceptable salt or hydrate thereof.

The invention further relates to methods for treating or preventing an inflammation disease, comprising administering to an animal in need thereof an effective amount of a compound of formula (Ic):

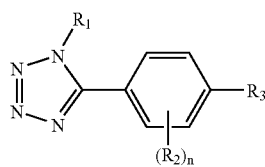

(Ic)

or a pharmaceutically acceptable salt or hydrate thereof, wherein:

$R_1$ is —H, —$CO_2R_4$, —C(O)$R_5$, or —C(O)N($R_5$)($R_5$);

each $R_2$ is independently -halo, —$NO_2$, —CN, —OH, —N($R_5$)($R_5$), —$OR_5$, —C(O)$R_5$, —OC(O)$R_5$, —C(O)NHC(O)$R_5$, —($C_1$–$C_{10}$)alkyl, —($C_2$–$C_{10}$)alkenyl, —($C_2$–$C_{10}$)alkynyl, —($C_3$–$C_{10}$)cycloalkyl, —($C_8$–$C_{14}$)bicycloalkyl, —($C_5$–$C_{10}$)cycloalkenyl, —($C_3$–$C_{10}$)heterocycle, —($C_5$)heteroaryl, —($C_6$)heteroaryl, -phenyl, -naphthyl, -benzyl, —$CO_2R_5$, —C(O)OCH($R_5$)($R_5$), —NHC(O)$R_5$, —NHC(O)NH$R_5$, —C(O)NH$R_5$, —OC(O)$R_5$, —OC(O)O$R_5$, —$SR_5$, —S(O)$R_5$, or —S(O)$_2R_5$;

$R_3$ is —H, -halo, —$NO_2$, —CN, —OH, —N($R_5$)($R_5$), —O($CH_2$)$_mR_5$, —C(O)$R_5$, —C(O)N($R_5$)($R_5$), —C(O)NH($CH_2$)$_m$($R_5$), —$OCF_3$, -benzyl, —$CO_2$CH($R_5$)($R_5$), —($C_1$–$C_{10}$)alkyl, —($C_2$–$C_{10}$)alkenyl, —($C_2$–$C_{10}$)alkynyl, —($C_3$–$C_{10}$)cycloalkyl, —($C_8$–$C_{14}$)bicycloalkyl, —($C_5$–$C_{10}$)cycloalkenyl, —($C_5$)heteroaryl, —($C_6$)heteroaryl, -naphthyl, —($C_3$–$C_{10}$)heterocycle, —$CO_2$($CH_2$)$_mR_5$, —NHC(O)$R_5$, —N($R_5$)C(O)$R_5$, —NHC(O)NH$R_5$, —OC(O)($CH_2$)$_m$CH$R_5R_5$, —$CO_2$($CH_2$)$_m$CH$R_5R_5$, —OC(O)O$R_5$, —$SR_5$, —S(O)$R_5$, —S(O)$_2R_5$, —S(O)$_2$NH$R_5$, or

$R_4$ is —$CF_3$, —($C_1$–$C_{10}$)alkyl, -benzyl, -adamantyl, -morpholinyl, -pyrrolidyl, -pyrridyloxide, -pyrrolidinyldione, -piperdidyl, —($C_5$)heteroaryl, —($C_6$)heteroaryl, —($C_2$–$C_{10}$)alkenyl, —($C_2$–$C_{10}$)alkynyl, —($C_3$–$C_{10}$)cycloalkyl, —($C_8$–$C_{14}$)bicycloalkyl, —($C_3$–$C_{10}$)heterocycle, or

each $R_5$ is independently —H or $R_4$;

each $R_6$ is independently —H, -halo, —$NO_2$, —CN, —OH, —$CO_2$H, —N(($C_1$–$C_{10}$)alkyl($C_1$–$C_{10}$)alkyl), —O($C_1$–$C_{10}$)alkyl, —C(O)($C_1$–$C_{10}$)alkyl, —C(O)NH($CH_2$)$_m$($C_1$–$C_{10}$)alkyl, —$OCF_3$, -benzyl, —$CO_2$($CH_2$)$_m$CH(($C_1$–$C_{10}$)alkyl($C_1$–$C_{10}$)alkyl), —C(O)H, —$CO_2$($C_1$–$C_{10}$)alkyl, —($C_1$–$C_{10}$)alkyl, —($C_2$–$C_{10}$)alkenyl, —($C_2$–$C_{10}$)alkynyl, —($C_3$–$C_{10}$)cycloalkyl, —($C_8$–$C_{14}$)bicycloalkyl, —($C_5$–$C_{10}$)cycloalkenyl, —($C_5$)heteroaryl, —($C_6$)heteroaryl, -phenyl, naphthyl, —($C_3$–$C_{10}$)heterocycle, —$CO_2$($CH_2$)$_m$($C_1$–$C_{10}$)alkyl, —$CO_2$($CH_2$)$_m$H, —NHC(O)($C_1$–$C_{10}$)alkyl, —NHC(O)NH($C_1$–$C_{10}$)alkyl, —OC(O)($C_1$–$C_{10}$)alkyl, —OC(O)O($C_1$–$C_{10}$)alkyl, —$SO_2$NH$R_5$, or —$SO_2NH_2$;

n is an integer ranging from 0 to 4;

each m is independently an integer ranging from 0 to 8; and each p is independently an integer ranging from 0 to 5.

The invention further relates to methods for treating or preventing a reperfusion disease, comprising administering to an animal in need thereof an effective amount of a compound of formula (Ic) or a pharmaceutically acceptable salt or hydrate thereof.

The invention further relates to methods for treating or preventing hyperuricemia, comprising administering to an animal in need thereof an effective amount of a compound of formula (Ic) or a pharmaceutically acceptable salt or hydrate thereof.

The invention further relates to methods for treating or preventing tumor-lysis syndrome, comprising administering to an animal in need thereof an effective amount of a compound of formula (Ic) or a pharmaceutically acceptable salt or hydrate thereof.

The invention further relates to methods for treating or preventing an inflammatory bowel disorder, comprising administering to an animal in need thereof an effective amount of a compound of formula (Ic) or a pharmaceutically acceptable salt or hydrate thereof.

The invention further relates to methods for inhibiting xanthine oxidase activity, comprising administering to an animal in need thereof an effective amount of a compound of formula (Ic) or a pharmaceutically acceptable salt or hydrate thereof.

The invention also relates to kits comprising a container containing a compound of formula (Ia), (Ib), or (Ic) or a pharmaceutically acceptable salt or hydrate thereof (each being a "5-Aryltetrazole Compound").

The invention can be understood more fully by reference to the following X detailed description and illustrative examples, which are intended to exemplify non-limiting embodiments of the invention.

4. DETAILED DESCRIPTION OF THE INVENTION

4.1. Definitions

As used herein, the term "—($C_1$–$C_{10}$)alkyl" means a saturated straight chain or branched non-cyclic hydrocarbon having from 1 to 10 carbon atoms. Representative saturated straight chain alkyls include -methyl, -ethyl, -n-propyl, -n-butyl, -n-pentyl, -n-hexyl, -n-heptyl, -n-octyl, -n-nonyl and -n-decyl; while saturated branched alkyls include -isopropyl, -sec-butyl, -isobutyl, -tert-butyl, -isopentyl, -2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimtheylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. In addition, chemical nomenclature used to define alkyl groups has its standard meaning known to those of ordinary skill in the art, for example, "Me" means methyl or —CH$_3$, "Et" means ethyl or —CH$_2$CH$_3$, "n-Pr" means n-propyl or —CH$_2$CH$_2$CH$_3$, "i-Pr" means iso-propyl or —CH(CH$_3$)$_2$, "n-Bu" means n-butyl or —CH$_2$(CH$_2$)$_2$CH$_3$, "t-Bu" means tert-butyl or —C(CH$_3$)$_3$.

As used herein, the term "—(C$_2$–C$_{10}$)alkenyl" means a straight chain or branched non-cyclic hydrocarbon having from 2 to 10 carbon atoms and including at least one carbon-carbon double bond. Representative straight chain and branched (C$_2$–C$_{10}$)alkenyls include -vinyl, -allyl, -1-butenyl, -2-butenyl, -isobutylenyl, -1-pentenyl, -2-pentenyl, -3-methyl-i-butenyl, -2-methyl-2-butenyl, 2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl and the like.

As used herein, the term "—(C$_2$–C$_{10}$)alkynyl" means a straight chain or branched non-cyclic hydrocarbon having from 2 to 10 carbon atoms and including at lease one carbon-carbon triple bond. Representative straight chain and branched —(C$_2$–C$_{10}$)alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, -1-nonynyl, -2-nonynyl, -8-nonynyl, -1-decynyl, -2-decynyl, -9-decynyl and the like.

As used herein, the term "—(C$_3$–C$_{10}$)cycloalkyl" means a saturated cyclic hydrocarbon having from 3 to 10 carbon atoms. Representative (C$_3$–C$_{10}$)cycloalkyls include -cyclopropyl, -cyclobutyl, -cyclopentyl, -cyclohexyl, -cycloheptyl, -cyclooctyl, -cyclononyl, and -cyclodecyl.

As used herein, the term "—(C$_8$–C$_{14}$)bicycloalkyl" means a bi-cyclic hydrocarbon ring system having from 8 to 14 carbon atoms and at least one saturated cyclic alkyl ring. Representative —(C$_8$–C$_{14}$)bicyclocycloalkyls include -indainyl, -1,2,3,4-tetrahydronaphthyl, -5,6,7,8-tetrahydronaphthyl, -perhydronaphthyl and the like.

As used herein, the term "—(C$_5$–C$_{10}$)cycloalkenyl" means a cyclic non-aromatic hydrocarbon having at least one carbon-carbon double bond in the cyclic system and from 5 to 10 carbon atoms. Representative (C$_5$–C$_{10}$)cycloalkenyls include -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl, -cyclononadienyl, -cyclodecenyl, -cyclodecadienyl and the like.

As used herein, the term "—(C$_3$–C$_{10}$)heterocycle" or "—(C$_3$–C$_{10}$)heterocyclo" means a 3- to 10-membered monocyclic heterocyclic ring which is either saturated, unsaturated non-aromatic, or aromatic. A 3-membered —(C$_3$–C$_7$)heterocycle can contain up to 3 heteroatoms, and a 4- to 10-membered —(C$_3$–C$_{10}$)heterocycle can contain up to 4 heteroatoms. Each heteroatom is independently selected from nitrogen, which can be quaternized; oxygen; and sulfur, including sulfoxide and sulfone. The —(C$_3$–C$_{10}$) heterocycle may be attached via any heteroatom or carbon atom. Representative —(C$_3$–C$_{10}$)heterocycles include pyridyl, furyl, thiophenyl, pyrrolyl, oxazolyl, imidazolyl, thiazolyl, isoxazolyl, pyrazolyl, isothiazolyl, pyridazinyl, pyrimidinyl, pyrazinyl, triazinyl, morpholinyl, pyrrolidinonyl, pyrrolidinyl, piperidinyl, piperazinyl, benzo[1,3]dioxolyl, hydantoinyl, valerolactamyl, oxiranyl, oxetanyl, tetrahydrofuranyl, tetrahydropyranyl, tetrahydropyrindinyl, tetrahydropyrimidinyl, tetrahydrothiophenyl, tetrahydrothiopyranyl, and the like. A heteroatom may be substituted with a protecting group known to those of ordinary skill in the art, for example, the hydrogen on a nitrogen may be substituted with a tert-butoxycarbonyl group or the hydrogen on an oxygen may be substituted with a methoxymethyl.

As used herein, the term "—(C$_5$)heteroaryl" means an aromatic heterocycle ring of 5 members, wherein at least one carbon atom of the ring is replaced with a heteroatom such as, for example, nitrogen. Representative —(C$_5$)heteroaryls include furyl, thienyl, pyrrolyl, oxazolyl, imidazolyl, thiazolyl, isoxazolyl, pyrazolyl, isothiazolyl, pyrazinyl, triazolyl, thiadiazolyl, and the like.

As used herein, the term "—(C$_6$)heteroaryl" means an aromatic heterocycle ring of 6 members, wherein at least one carbon atom of the ring is replaced with a heteroatom such as, for example, nitrogen. One of the —(C$_6$)heteroaryl's rings contain at least one carbon atom. Representative (C$_6$)heteroaryls include pyridyl, pyridazinyl, pyrazinyl, triazinyl, tetrazinyl, pyrimidyl, and the like.

As used herein, the term "—O(C$_1$–C$_{10}$)alkyl" means a saturated straight chain or branched non-cyclic hydrocarbon having from 1 to 10 carbon atoms. Representative saturated straight chain alkyls include -methyoxy, -ethyoxy, -n-propyloxy, -n-butyloxy, -n-pentyloxy, -n-hexyloxy, -n-heptyloxy, -n-octyloxy, -n-nonyloxy and -n-decyloxy; while saturated branched alkyls include -isopropyloxy, -sec-butyloxy, -isobutyloxy, -tert-butyloxy, -isopentyloxy, -2-methylbutyloxy, -3-methylbutyloxy, -2-methylpentyloxy, -3-methylpentyloxy, -4-methylpentyloxy, -2-methylhexyloxy, -3-methylhexyloxy, -4-methylhexyloxy, -5-methylhexyloxy, -2,3-dimethylbutyloxy, -2,3-dimethylpentyloxy, -2,4-dimethylpentyloxy, -2,3-dimethylhexyloxy, -2,4-dimethylhexyloxy, -2,5-dimethylhexyloxy, 2,2-dimethylpentyloxy, -2,2-dimethylpentyloxy, -3,3-dimtheylpentyloxy, -3,3-dimethylhexyloxy, -4,4-dimethylhexyloxy, -2-ethylpentyloxy, -3-ethylpentyloxy, -2-ethylhexyloxy, -3-ethylhexyloxy, -4-ethylhexyloxy, -2-methyl-2-ethylpentyloxy, -2-methyl-3-ethylpentyloxy, -2-methyl -4-ethylpentyloxy, -2-methyl-2-ethylhexyloxy, -2-methyl-3-ethylhexyloxy, -2-methyl-4-ethylhexyloxy, -2,2-diethylpentyloxy, -3,3-diethylhexyloxy, -2,2-diethylhexyloxy, -3,3-diethylhexyloxy and the like. In addition, chemical nomenclature used to define alkyloxy groups has its standard meaning known to those of ordinary skill in the art, for example, "OMe" means methoxy, methoxyl, or —OCH$_3$, "OEt" means ethoxy, ethoxyl, or —OCH$_2$CH$_3$, "n-OPr" means n-propyloxy or —CH$_2$CH$_2$CH$_3$, "i-OPr"

means iso-propyloxy or —OCH(CH$_3$)$_2$, "n-OBu" means n-butyloxy or —OCH$_2$(CH$_2$)$_2$CH$_3$, "t-OBu" means tert-butyloxy or —OC(CH$_3$)$_3$.

As used herein, the term "-Halogen" or "-Halo" means —F, —Cl, —Br or —I.

As used herein, the term "animal," includes, but is not limited to, a cow, monkey, chimpanzee, baboon, horse, sheep, pig, chicken, turkey, quail, cat, dog, mouse, rat, rabbit, guinea pig and human.

As used herein, the term "adamantyl" includes 1-adamantyl, 2-adamantyl, and 3-adamantyl.

As used herein, the term "naphthyl" includes 1-naphthyl and 2-naphthyl.

As used herein, the term "morpholinyl" includes N-morpholinyl, 2-morpholinyl, and 3-morpholinyl.

As used herein, the term "pyrridyloxide" includes 2-pyrridyloxide, 3-pyrridyloxide, and 4-pyrridyloxide.

As used herein, the term "pyrrolidinyldione" includes N-pyrrolidinyl-2,3-dione, N-pyrrolidinyl-2,4-dione, N-pyrrolidinyl-2,5-dione, N-pyrrolidinyl-3,5-dione, N-pyrrolidinyl-3,4-dione, 2-pyrrolidinyl-3,4-dione, or 3-pyrrolidinyldione-2,4-dione, and 3-pyrrolidinyl-2,5-dione.

As used herein, the term "piperdinyl" includes N-piperdinyl, 2-piperdinyl, and 3-piperdinyl.

As used herein, the term "pharmaceutically acceptable salt," is a salt formed from an acid and a basic nitrogen group of one of the 5-Aryltetrazole Compounds. Illustrative salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, fornate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also refers to a salt prepared from a 5-Aryltetrazole Compound having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)amine, or tri-(2-hydroxyethyl))-amine; and amino acids such as arginine, lysine, and the like.

As used herein, the term "pharmaceutically acceptable hydrate," is a hydrate formed from the association of one or more water molecules with a 5-Aryltetrazole Compound. The term "hydrate" includes a mono-hydrate, dihydrate, trihydrate, tetrahydrate, and the like.

As used herein in connection with a 5-Aryltetrazole Compound, the term "effective amount" means an amount effective for: (a) treating or preventing an inflammation disease, a reperfusion disease, or hyperuricemia; or (b) inhibiting xanthine oxidase activity.

4.2. Compounds of Formula (Ia)

As stated above, the invention encompasses compounds of formula (Ia):

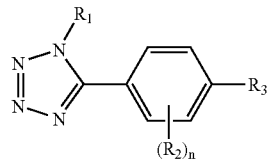

and pharmaceutically acceptable salts and hydrates thereof, wherein $R_1$, $R_2$, $R_3$, and n are defined above for the compounds of formula (Ia).

In one embodiment n is 0.

In another embodiment n is 0 and $R_3$ is -halo.

In another embodiment n is 0 and $R_3$ is —C(O)R$_5$,

In another embodiment n is 0 and $R_3$ is —C(O)NHC(O)R$_5$.

In another embodiment n is 0 and $R_3$ is —C(O)N(R$_5$)(R$_5$).

In another embodiment n is 0 and $R_3$ is —CO$_2$(CH$_2$)$_m$(R$_5$).

In another embodiment n is 0 and $R_3$ is —H.

In another embodiment n is 0 and $R_3$ is —NHC(O)N(R$_5$)(R$_5$).

In another embodiment n is 0 and $R_3$ is —C(O)NHR$_5$.

In another embodiment n is 0; $R_3$ is —C(O)NHR$_5$; and $R_5$ is

In another embodiment n is 0; $R_3$ is —C(O)NHR$_5$; $R_5$ is

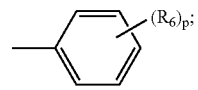

and p is an integer from 1 to 3.

In another embodiment n is 0; $R_3$ is —C(O)NHR$_5$; $R_5$ is

and p is 1 or 2.

In another embodiment n is 0; $R_3$ is —C(O)NHR$_5$; $R_5$ is

p is 1; and $R_6$ is in the para position.

In another embodiment n is 0; $R_3$ is —C(O)NHR$_5$; $R_5$ is

p is 1; and $R_6$ is in a meta position.

In another embodiment n is 0; $R_3$ is —C(O)NHR$_5$; $R_5$ is

p is 1; and $R_6$ is in an ortho position.

In another embodiment n is 0; $R_3$ is —C(O)NHR$_5$; $R_5$ is

and each $R_6$ is independently -halo.

In another embodiment n is 0; $R_3$ is —C(O)NHR$_5$; $R_5$ is

p is 2; and each $R_6$ is independently -halo.

In another embodiment n is 0; $R_3$ is —C(O)NHR$_5$; $R_5$ is

p is 2; each $R_6$ is independently halo; and one $R_6$ is in the para position and the other $R_6$ is in a meta position.

In another embodiment n is 0; $R_3$ is —C(O)NHR$_5$; $R_5$ is

p is 2; each $R_6$ is independently halo; and one $R_6$ is in the para position and the other $R_6$ is in an ortho position.

In another embodiment n is 0; $R_3$ is —C(O)NHR$_5$; $R_5$ is

p is 2; each $R_6$ is independently halo; and one $R_6$ is in an ortho position and the other $R_6$ is in a meta position.

In another embodiment n is 0; $R_3$ is —C(O)NHR$_5$; $R_5$ is

p is 2; each $R_6$ is independently halo; and each $R_6$ is in an ortho position.

In another embodiment n is 0; $R_3$ is —C(O)NHR$_5$; $R_5$ is

p is 2; each $R_6$ is independently halo; and each $R_6$ is in a meta position.

Illustrative subclasses of the compounds of formula (Ia) have the following formulas, wherein $R_4$ is —(C$_5$)heteroaryl, —(C$_6$)heteroaryl, phenyl, naphthyl, or benzyl:

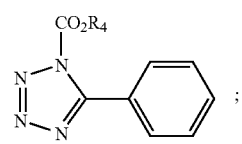

Formula AA

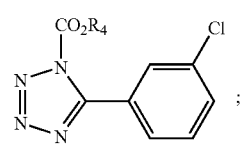

Formula AB

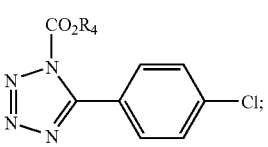

Formula AC

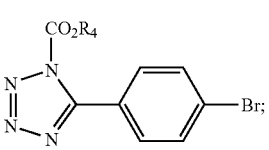

Formula AD

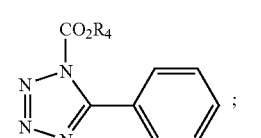

Formula AE

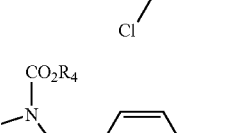

Formula AF

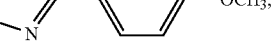

Formula AG

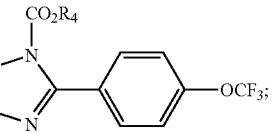

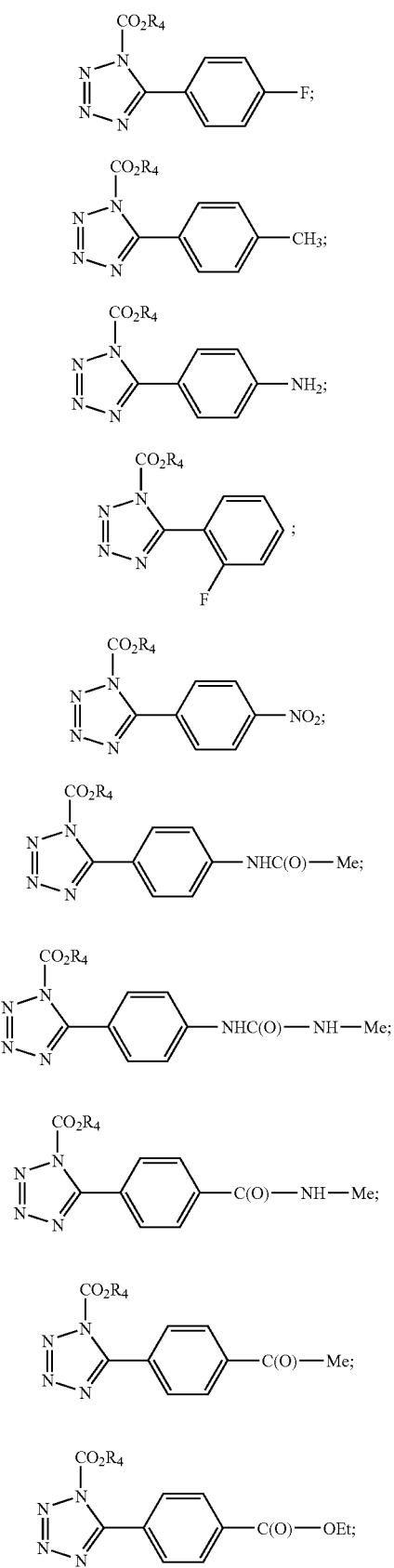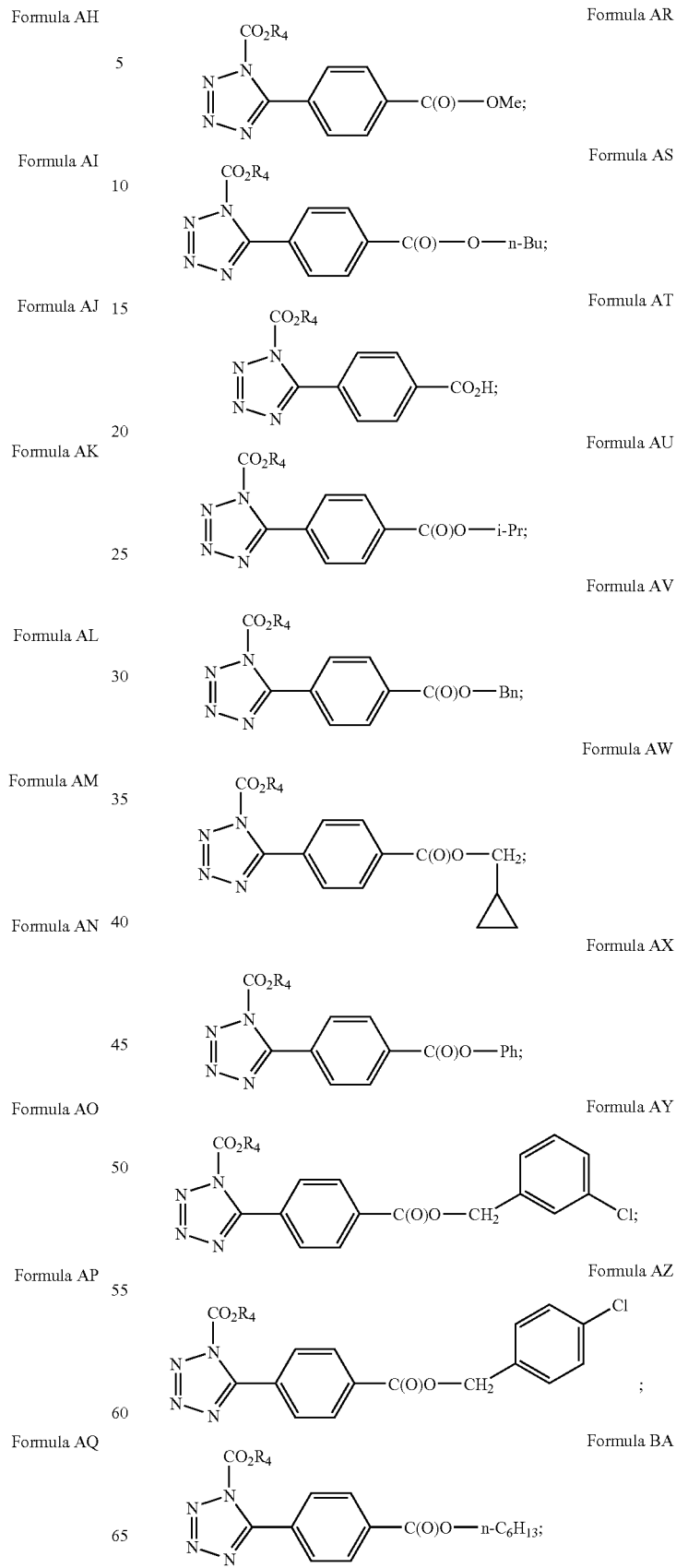

Formula BB: tetrazole-C₆H₄-C(O)O-n-C₈H₁₇ with CO₂R₄ on tetrazole N

Formula BC: tetrazole-C₆H₄-C(O)O-cyclohexyl with CO₂R₄

Formula BD: tetrazole-C₆H₄-C(O)OCH₂-adamantyl with CO₂R₄

Formula BE: tetrazole-C₆H₄-C(O)OCH₂CF₃ with CO₂R₄

Formula BF: tetrazole-C₆H₄-C(O)OCH₂CH₂-morpholinyl with CO₂R₄

Formula BG: tetrazole-C₆H₄-C(O)OCH₂CH₂-pyrrolidinyl with CO₂R₄

Formula BH: tetrazole-C₆H₄-C(O)O-CH₂CH₂CH₂C≡CH with CO₂R₄

Formula BI: tetrazole-C₆H₄-C(O)O-(pyridinyl N-oxide) with CO₂R₄

Formula BJ: tetrazole-C₆H₄-C(O)O-cyclohexyl with CO₂R₄

Formula BK: tetrazole-C₆H₄-C(O)O-CH₂CF₂CF₂H with CO₂R₄

Formula BL: tetrazole-C₆H₄-C(O)O-CH₂C≡C-CH₂CH₃ with CO₂R₄

Formula BM: tetrazole-C₆H₄-C(O)O-CH₂-(4-isopropenyl-cyclohexenyl) with CO₂R₄

Formula BN: tetrazole-C₆H₄-C(O)O-CH₂CH(CF₃)(CF₃) with CO₂R₄

Formula BO: tetrazole-C₆H₄-C(O)O-(3-bromophenyl) with CO₂R₄

Formula BP: tetrazole-C₆H₄-C(O)O-(4-bromophenyl) with CO₂R₄

Formula BQ: tetrazole-C₆H₄-C(O)O-CH₂CCl₃ with CO₂R₄

Formula BR: tetrazole-C₆H₄-C(O)O-CH₂CH₂-(2,5-dioxopyrrolidinyl) with CO₂R₄

Formula BS: tetrazole-C₆H₄-C(O)O-CH₂-(2-iodophenyl) with CO₂R₄

-continued

Formula BT

Formula BU

Formula BV

Formula BW

Formula BX

Formula BY

Formula BZ

Formula CA

Formula CB

-continued

Formula CC

Formula CD

Formula CE

Formula CF

Formula CG

Formula CH

Formula CI

Formula CJ

-continued

Formula CK

Formula CL

Formula CM

Formula CN

Formula CO

Formula CP

Formula CQ

Formula CR

Formula CS

-continued

Formula CT

Formula CU

Formula CV

Formula CW

Formula CX

Formula CY

Formula CZ

Formula DA

Formula DB

-continued

Formula DC

Formula DD

Formula DE

Formula DF

Formula DG

Formula DH

Formula DI

Formula DJ

Formula DK

Formula DL

Formula DM

Formula DN

Formula DO

Formula DP

Formula DQ

Formula DR

Formula DS and pharmaceutically acceptable salts or hydrates thereof.

4.3. Compounds of Formula (Ib)

The invention also encompasses compounds of formula (Ib):

(Ib)

and pharmaceutically acceptable salts and hydrates thereof, wherein $R_1$ and $R_2$ are defined above for the compounds of formula (Ib).

In one embodiment $R_1$ is —H.

In another embodiment $R_1$ is —H and $R_2$ is —$(C_1-C_{10})$ alkyl.

In another embodiment R$_1$ is —H and R$_2$ is —O(C$_1$–C$_{10}$) alkyl.

In another embodiment, R$_1$ is —H and R$_2$ is methyl.
In another embodiment, R$_1$ is —H and R$_2$ is ethyl.
In another embodiment, R$_1$ is —H and R$_2$ is n-propyl.
In another embodiment, R$_1$ is —H and R$_2$ is iso-propyl.
In another embodiment, R$_1$ is —H and R$_2$ is n-butyl.
In another embodiment, R$_1$ is —H and R$_2$ is iso-butyl.
In another embodiment, R$_1$ is —H and R$_2$ is sec-butyl.
In another embodiment, R$_1$ is —H and R$_2$ is tert-butyl.
In another embodiment, R$_1$ is —H and R$_2$ is n-pentyl.
In another embodiment, R$_1$ is —H and R$_2$ is isopentyl.
In another embodiment, R$_1$ is —H and R$_2$ is n-hexyl.
In another embodiment, R$_1$ is —H and R$_2$ is n-heptyl.
In another embodiment, R$_1$ is —H and R$_2$ is n-octyl.
In another embodiment, R$_1$ is —H and R$_2$ is n-nonyl.
In another embodiment, R$_1$ is —H and R$_2$ is n-decyl.
In another embodiment, R$_1$ is —H and R$_2$ is 2-methylbutyl.
In another embodiment, R$_1$ is —H and R$_2$ is 3-methylbutyl.
In another embodiment, R$_1$ is —C(O)R$_5$ and R$_2$ is methyl.
In another embodiment, R$_1$ is —C(O)R$_5$ and R$_2$ is ethyl.
In another embodiment, R$_1$ is —C(O)R$_5$ and R$_2$ is n-propyl.
In another embodiment, R$_1$ is —C(O)R$_5$ and R$_2$ is iso-propyl.
In another embodiment, R$_1$ is —C(O)R$_5$ and R$_2$ is n-butyl.
In another embodiment, R$_1$ is —C(O)R$_5$ and R$_2$ is iso-butyl.
In another embodiment, R$_1$ is —C(O)R$_5$ and R$_2$ is sen-butyl.
In another embodiment, R$_1$ is —C(O)R$_5$ and R$_2$ is tert-butyl.
In another embodiment, R$_1$ is —C(O)R$_5$ and R$_2$ is n-pentyl.
In another embodiment, R$_1$ is —C(O)R$_5$ and R$_2$ is iso-pentyl.
In another embodiment, R$_1$ is —C(O)R$_5$ and R$_2$ is n-hexyl.
In another embodiment, R$_1$ is —C(O)R$_5$ and R$_2$ is n-heptyl.
In another embodiment, R$_1$ is —C(O)R$_5$ and R$_2$ is n-octyl.
In another embodiment, R$_1$ is —C(O)R$_5$ and R$_2$ is n-nonyl.
In another embodiment, R$_1$ is —C(O)R$_5$ and R$_2$ is n-decyl.
In another embodiment, R$_1$ is —C(O)R$_5$ and R$_2$ is 2-methylbutyl.
In another embodiment, R$_1$ is —C(O)R$_5$ and R$_2$ is 3-methylbutyl.
In another embodiment, R$_1$ is —CO$_2$R$_4$ and R$_2$ is methyl.
In another embodiment, R$_1$ is —CO$_2$R$_4$ and R$_2$ is ethyl.
In another embodiment, R$_1$ is —CO$_2$R$_4$ and R$_2$ is n-propyl.
In another embodiment, R$_1$ is —CO$_2$R$_4$ and R$_2$ is iso-propyl.
In another embodiment, R$_1$ is —CO$_2$R$_4$ and R$_2$ is n-butyl.
In another embodiment, R$_1$ is —CO$_2$R$_4$ and R$_2$ is iso-butyl.
In another embodiment, R$_1$ is —CO$_2$R$_4$ and R$_2$ is sec-butyl.
In another embodiment, R$_1$ is —CO$_2$R$_4$ and R$_2$ is tert-butyl.
In another embodiment, R$_1$ is —CO$_2$R$_4$ and R$_2$ is n-pentyl.
In another embodiment, R$_1$ is —CO$_2$R$_4$ and R$_2$ is isopentyl.
In another embodiment, R$_1$ is —CO$_2$R$_4$ and R$_2$ is n-hexyl.
In another embodiment, R$_1$ is —CO$_2$R$_4$ and R$_2$ is n-heptyl.
In another embodiment, R$_1$ is —CO$_2$R$_4$ and R$_2$ is n-octyl.
In another embodiment, R$_1$ is —CO$_2$R$_4$ and R$_2$ is n-nonyl.
In another embodiment, R$_1$ is —CO$_2$R$_4$ and R$_2$ is n-decyl.
In another embodiment, R$_1$ is —CO$_2$R$_4$ and R$_2$ is 2-methylbutyl.
In another embodiment, R$_1$ is —CO$_2$R$_4$ and R$_2$ is 3-methylbutyl.
In another embodiment, R$_1$ is —C(O)N(R$_5$)(R$_5$) and R$_2$ is methyl.
In another embodiment, R$_1$ is —C(O)N(R$_5$)(R$_5$) and R$_2$ is ethyl.
In another embodiment, R$_1$ is —C(O)N(R$_5$)(R$_5$) and R$_2$ is n-propyl.
In another embodiment, R$_1$ is —C(O)N(R$_5$)(R$_5$) and R$_2$ is iso-propyl.
In another embodiment, R$_1$ is —C(O)N(R$_5$)(R$_5$) and R$_2$ is n-butyl.
In another embodiment, R$_1$ is —C(O)N(R$_5$)(R$_5$) and R$_2$ is iso-butyl.
In another embodiment, R$_1$ is —C(O)N(R$_5$)(R$_5$) and R$_2$ is sec-butyl.
In another embodiment, R$_1$ is —C(O)N(R$_5$)(R$_5$) and R$_2$ is tert-butyl.
In another embodiment, R$_1$ is —C(O)N(R$_5$)(R$_5$) and R$_2$ is n-pentyl.
In another embodiment, R$_1$ is —C(O)N(R$_5$)(R$_5$) and R$_2$ is isopentyl.
In another embodiment, R$_1$ is —C(O)N(R$_5$)(R$_5$) and R$_2$ is n-hexyl.
In another embodiment, R$_1$ is —C(O)N(R$_5$)(R$_5$) and R$_2$ is n-heptyl.
In another embodiment, R$_1$ is —C(O)N(R$_5$)(R$_5$) and R$_2$ is n-octyl.
In another embodiment, R$_1$ is —C(O)N(R$_5$)(R$_5$) and R$_2$ is n-nonyl.
In another embodiment, R$_1$ is —C(O)N(R$_5$)(R$_5$) and R$_2$ is n-decyl.
In another embodiment, R$_1$ is —C(O)N(R$_5$)(R$_5$) and R$_2$ is 2-methylbutyl.
In another embodiment, R$_1$ is —C(O)N(R$_5$)(R$_5$) and R$_2$ is 3-methylbutyl.
In another embodiment, R$_1$ is —H and R$_2$ is methoxy.
In another embodiment, R$_1$ is —H and R$_2$ is ethoxy.
In another embodiment, R$_1$ is —H and R$_2$ is n-propyloxy.
In another embodiment, R$_1$ is —H and R$_2$ is iso-propyloxy.
In another embodiment, R$_1$ is —H and R$_2$ is n-butyloxy.
In another embodiment, R$_1$ is —H and R$_2$ is iso-butyloxy.
In another embodiment, R$_1$ is —H and R$_2$ is sec-butyloxy.
In another embodiment, R$_1$ is —H and R$_2$ is tert-butyloxy.
In another embodiment, R$_1$ is —H and R$_2$ is n-pentyloxy.
In another embodiment, R$_1$ is —H and R$_2$ is isopentyloxy.
In another embodiment, R$_1$ is —H and R$_2$ is n-hexyloxy.
In another embodiment, R$_1$ is —H and R$_2$ is n-heptyloxy.
In another embodiment, R$_1$ is —H and R$_2$ is n-octyloxy.
In another embodiment, R$_1$ is —H and R$_2$ is n-nonyloxy.
In another embodiment, R$_1$ is —H and R$_2$ is n-decyloxy.
In another embodiment, R$_1$ is —H and R$_2$ is 2-methyloxy.
In another embodiment, R$_1$ is —H and R$_2$ is 3-methylbutyloxy.
In another embodiment, R$_1$ is —C(O)R$_5$ and R$_2$ is methoxy.
In another embodiment, R$_1$ is —C(O)R$_5$ and R$_2$ is ethoxy.

In another embodiment, $R_1$ is —C(O)$R_5$ and $R_2$ is n-propyloxy.

In another embodiment, $R_1$ is —C(O)$R_5$ and $R_2$ is iso-propyloxy.

In another embodiment, $R_1$ is —C(O)$R_5$ and $R_2$ is n-butyloxy.

In another embodiment, $R_1$ is —C(O)$R_5$ and $R_2$ is iso-butyloxy.

In another embodiment, $R_1$ is —C(O)$R_5$ and $R_2$ is sec-butyloxy.

In another embodiment, $R_1$ is —C(O)$R_5$ and $R_2$ is tert-butyloxy.

In another embodiment, $R_1$ is —C(O)$R_5$ and $R_2$ is n-pentyloxy.

In another embodiment, $R_1$ is —C(O)$R_5$ and $R_2$ is iso-pentyloxy.

In another embodiment, $R_1$ is —C(O)$R_5$ and $R_2$ is n-hexyloxy.

In another embodiment, $R_1$ is —C(O)$R_5$ and $R_2$ is n-heptyloxy.

In another embodiment, $R_1$ is —C(O)$R_5$ and $R_2$ is n-octyloxy.

In another embodiment, $R_1$ is —C(O)$R_5$ and $R_2$ is n-nonyloxy.

In another embodiment, $R_1$ is —C(O)$R_5$ and $R_2$ is n-decyloxy.

In another embodiment, $R_1$ is —C(O)$R_5$ and $R_2$ is 2-methylyoxy.

In another embodiment, $R_1$ is —C(O)$R_5$ and $R_2$ is 3-methylbutyloxy.

In another embodiment, $R_1$ is —CO$_2$$R_4$ and $R_2$ is methoxy.

In another embodiment, $R_1$ is —CO$_2$$R_4$ and $R_2$ is ethoxy.

In another embodiment, $R_1$ is —CO$_2$$R_4$ and $R_2$ is n-propyloxy.

In another embodiment, $R_1$ is —CO$_2$$R_4$ and $R_2$ is iso-propyloxy.

In another embodiment, $R_1$ is —CO$_2$$R_4$ and $R_2$ is n-butyloxy.

In another embodiment, $R_1$ is —CO$_2$$R_4$ and $R_2$ is iso-butyloxy.

In another embodiment, $R_1$ is —CO$_2$$R_4$ and $R_2$ is sec-butyloxy.

In another embodiment, $R_1$ is —CO$_2$$R_4$ and $R_2$ is tert-butyloxy.

In another embodiment, $R_1$ is —CO$_2$$R_4$ and $R_2$ is n-pentyloxy.

In another embodiment, $R_1$ is —CO$_2$$R_4$ and $R_2$ is isopentyloxy.

In another embodiment, $R_1$ is —CO$_2$$R_4$ and $R_2$ is n-hexyloxy.

In another embodiment, $R_1$ is —CO$_2$$R_4$ and $R_2$ is n-heptyloxy.

In another embodiment, $R_1$ is —CO$_2$$R_4$ and $R_2$ is n-octyloxy.

In another embodiment, $R_1$ is —CO$_2$$R_4$ and $R_2$ is n-nonyloxy.

In another embodiment, $R_1$ is —CO$_2$$R_4$ and $R_2$ is n-decyloxy.

In another embodiment, $R_1$ is —CO$_2$$R_4$ and $R_2$ is 2-methylbutyloxy.

In another embodiment, $R_1$ is —CO$_2$$R_4$ and $R_2$ is 3-methylyoxy.

In another embodiment, $R_1$ is —C(O)N($R_5$)($R_5$) and $R_2$ is methyloxy.

In another embodiment, $R_1$ is —C(O)N($R_5$)($R_5$) and $R_2$ is ethyloxy.

In another embodiment, $R_1$ is —C(O)N($R_5$)($R_5$) and $R_2$ is n-propyloxy.

In another embodiment, $R_1$ is —C(O)N($R_5$)($R_5$) and $R_2$ is iso-propyloxy.

In another embodiment, $R_1$ is —C(O)N($R_5$)($R_5$) and $R_2$ is n-butyloxy.

In another embodiment, $R_1$ is —C(O)N($R_5$)($R_5$) and $R_2$ is iso-butyloxy.

In another embodiment, $R_1$ is —C(O)N($R_5$)($R_5$) and $R_2$ is sec-butyloxy.

In another embodiment, $R_1$ is —C(O)N($R_5$)($R_5$) and $R_2$ is tert-butyloxy.

In another embodiment, $R_1$ is —C(O)N($R_5$)($R_5$) and $R_2$ is n-pentyloxy.

In another embodiment, $R_1$ is —C(O)N($R_5$)($R_5$) and $R_2$ is isopentyloxy.

In another embodiment, $R_1$ is —C(O)N($R_5$)($R_5$) and $R_2$ is n-hexyloxy.

In another embodiment, $R_1$ is —C(O)N($R_5$)($R_5$) and $R_2$ is n-heptyloxy.

In another embodiment, $R_1$ is —C(O)N($R_5$)($R_5$) and $R_2$ is n-octyloxy.

In another embodiment, $R_1$ is —C(O)N($R_5$)($R_5$) and $R_2$ is n-nonyloxy.

In another embodiment, $R_1$ is —C(O)N($R_5$)($R_5$) and $R_2$ is n-decyloxy.

In another embodiment, $R_1$ is —C(O)N($R_5$)($R_5$) and $R_2$ is 2-methylbutyloxy.

In another embodiment, $R_1$ is —C(O)N($R_5$)($R_5$) and $R_2$ is 3-methylyoxy.

Illustrative compounds of formula (Ib) are:

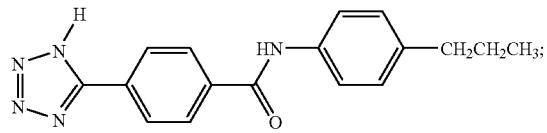

Compound EH

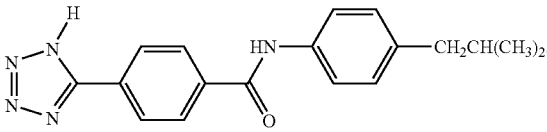

Compound EI

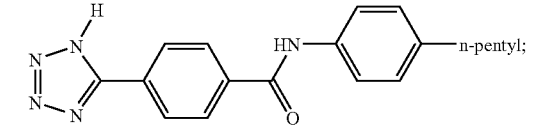

Comound EJ

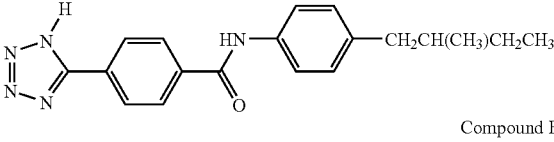

Compound EK

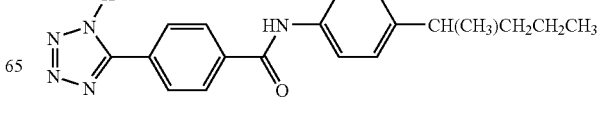

Compound EL

-continued

Compound EM: 5-(4-(N-(4-isobutylphenyl)carbamoyl)phenyl)-1H-tetrazole — tetrazole–C₆H₄–C(O)NH–C₆H₄–CH₂CH₂CH(CH₃)₂;

Compound EN: tetrazole–C₆H₄–C(O)NH–C₆H₄–n-hexyl;

Compound EO: tetrazole–C₆H₄–C(O)NH–C₆H₄–n-heptyl;

Compound EP: tetrazole–C₆H₄–C(O)NH–C₆H₄–n-octyl;

Compound EQ: tetrazole–C₆H₄–C(O)NH–C₆H₄–n-nonyl;

Compound ER: tetrazole–C₆H₄–C(O)NH–C₆H₄–n-decyl;

Compound ES: tetrazole–C₆H₄–C(O)NH–C₆H₄–OCH₂CH₃;

Compound ET: tetrazole–C₆H₄–C(O)NH–C₆H₄–OCH₂CH₂CH₃;

Compound EU: tetrazole–C₆H₄–C(O)NH–C₆H₄–OCH(CH₃)₂;

Compound EV: tetrazole–C₆H₄–C(O)NH–C₆H₄–O(n-butyl);

Compound EW: tetrazole–C₆H₄–C(O)NH–C₆H₄–OCH₂CH(CH₃)₂;

Compound EX: tetrazole–C₆H₄–C(O)NH–C₆H₄–O-(tert-butyl);

Compound EY: tetrazole–C₆H₄–C(O)NH–C₆H₄–O-(n-pentyl);

Compound EZ: tetrazole–C₆H₄–C(O)NH–C₆H₄–OCH₂CH₂CH(CH₃)₂;

Compound FA: tetrazole–C₆H₄–C(O)NH–C₆H₄–O(n-hexyl);

Compound FB: tetrazole–C₆H₄–C(O)NH–C₆H₄–O(n-heptyl);

Compound FC: tetrazole–C₆H₄–C(O)NH–C₆H₄–O-(n-octyl);

Compound FD: tetrazole–C₆H₄–C(O)NH–C₆H₄–O-(n-nonyl);

Compound FE: tetrazole–C₆H₄–C(O)NH–C₆H₄–O-(n-decyl);

and pharmaceutically acceptable salts and hydrates thereof.

4.4. Compounds of Formula (Ic)

As stated above, the invention further relates to methods for treating or preventing an inflammation disease, a reperfusion disease, or hyperuricemia comprising administering to an animal in need thereof an effective amount of a compound of formula (Ic):

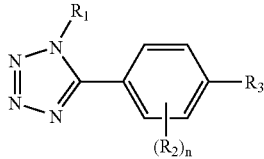

or a pharmaceutically acceptable salt or hydrate thereof, wherein $R_1$, $R_2$, $R_3$ and n are defined above for the compounds of formula (Ic).

In one embodiment $R_1$ is —H.

In another embodiment $R_1$ is —H; n is 0; and $R_3$ is —($C_1$–$C_{10}$)alkyl.

In another embodiment $R_1$ is —H; n is 0; and $R_3$ is —O(CH$_2$)$_m$R$_5$.

In another embodiment $R_1$ is —H; n is 0; $R_3$ is —O(CH$_2$)$_m$R$_5$; and $R_5$ is —H.

In another embodiment $R_1$ is —H; n is 0; and $R_3$ is -halo.

In another embodiment $R_1$ is —H; n is 0; and $R_3$ is —C(O)R$_5$.

In another embodiment $R_1$ is —H; n is 0; and $R_3$ is —C(O)NHC(O)R$_5$.

In another embodiment $R_1$ is —H; n is 0; and $R_3$ is —C(O)N(R$_5$)(R$_5$).

In another embodiment $R_1$ is —H; n is 0; and $R_3$ is —H.

In another embodiment $R_1$ is —H; n is 0; and $R_3$ is —CO$_2$(CH$_2$)$_m$(R$_5$).

In another embodiment $R_1$ is —H; n is 0; and $R_3$ is —NH$_C$(O)$_N$(R$_5$)(R$_5$).

In another embodiment $R_1$ is —H; n is 0; and $R_3$ is —C(O)NHR$_5$.

In another embodiment $R_1$ is —H; n is 0; $R_3$ is —C(O)NHR$_5$; and $R_5$ is

and p is an integer from 1 to 3.

In another embodiment $R_1$ is —H; n is 0; $R_3$ is —C(O)NHR$_5$; $R_5$ is

and p is 1 or 2.

In another embodiment $R_1$ is —H; n is 0; $R_3$ is —C(O)NHR$_5$; $R_5$ is

p is 1; and $R_6$ is halo and is in the para position.

In another embodiment $R_1$ is —H; n is 0; $R_3$ is —C(O)NHR$_5$; $R_5$ is

p is 1; and $R_6$ is halo and is in a meta position.

In another embodiment $R_1$ is —H; n is 0; $R_3$ is —C(O)NHR$_5$; $R_5$ is

p is 1; and $R_6$ is halo and is in an ortho position.

In another embodiment $R_1$ is —H; n is 0; $R_3$ is —C(O)NHR$_5$; $R_5$ is

p is 2; and each $R_6$ is independently -halo.

In another embodiment $R_1$ is —H; n is 0; $R_3$ is —C(O)NHR$_5$; $R_5$ is

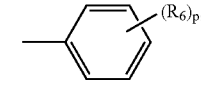

p is 2; each $R_6$ is independently -halo; and one $R_6$ is in the para position and the other $R_6$ is in a meta position.

In another embodiment $R_1$ is —H; n is 0; $R_3$ is —C(O)NHR$_5$; $R_5$ is

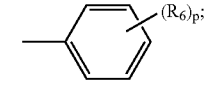

p is 2; each $R_6$ is independently -halo; and one $R_6$ is in the para position and the other $R_6$ is in an ortho position.

In another embodiment $R_1$ is —H; n is 0; $R_3$ is —C(O)NHR$_5$; $R_5$ is

p is 2; and one $R_6$ is in an ortho position and the other $R_6$ is in a meta position.

In another embodiment, $R_1$ is —CO$_2$R$_4$.

In another embodiment $R_1$ is —CO$_2$R$_4$ and n is 0.

In another embodiment $R_1$ is —CO$_2$R$_4$; n is 0; and $R_3$ is -halo.

In another embodiment $R_1$ is —CO$_2$R$_4$; n is 0; and $R_3$ is —C(O)R$_5$.

In another embodiment $R_1$ is —CO$_2$R$_4$; n is 0; and $R_3$ is —C(O)NHC(O)R$_5$.

In another embodiment $R_1$ is —CO$_2$R$_4$; n is 0; and $R_3$ is —H.

In another embodiment $R_1$ is —CO$_2$R$_4$; n is 0; and $R_3$ is —CO$_2$(CH$_2$)$_m$(R$_5$).

In another embodiment $R_1$ is —CO$_2$R$_4$; n is 0; and $R_3$ is —NHC(O)N(R$_5$)(R$_5$).

In another embodiment $R_1$ is —CO$_2$R$_4$; n is 0; and $R_3$ is —C(O)N(R$_5$)(R$_5$).

In another embodiment $R_1$ is —CO$_2$R$_4$; n is 0; and $R_3$ is —C(O)NHR$_5$.

In another embodiment $R_1$ is —CO$_2$R$_4$; n is 0; $R_3$ is —C(O)NHR$_5$; and $R_5$ is

In another embodiment $R_1$ is —CO$_2$R$_4$; n is 0; $R_3$ is —C(O)NHR$_5$; $R_5$ is

and p is an integer from 1 to 3.

In another embodiment $R_1$ is —CO$_2$R$_4$; n is 0; $R_3$ is —C(O)NHR$_5$; $R_5$ is

and p is 1 or 2.

In another embodiment $R_1$ is —CO$_2$R$_4$; n is 0; $R_3$ is —C(O)NHR$_5$; $R_5$ is

p is 1; and $R_6$ is halo and is in the para position.

In another embodiment $R_1$ is —CO$_2$R$_4$; n is 0; $R_3$ is —C(O)NHR$_5$; $R_5$ is

p is 1, and $R_6$ is halo and is in a meta position.

In another embodiment $R_1$ is —CO$_2$R$_4$; n is 0; $R_3$ is —C(O)NHR$_5$; $R_5$ is

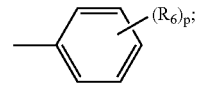

p is 1, and $R_6$ is halo and is in an ortho position.

In another embodiment $R_1$ is —CO$_2$R$_4$; n is 0; $R_3$ is —C(O)NHR$_5$; $R_5$ is

p is 2; and each $R_6$ is independently -halo.

In another embodiment $R_1$ is —CO$_2$R$_4$; n is 0; $R_3$ is —C(O)NHR$_5$; $R_5$ is

p is 2; each $R_6$ is independently halo; and one $R_6$ is in the para position and the other $R_6$ is in a meta position.

In another embodiment $R_1$ is —CO$_2$R$_4$; n is 0; $R_3$ is —C(O)NHR$_5$; $R_5$ is

p is 2; each $R_6$ is independently halo; and one $R_6$ is in the para position and the other $R_6$ is in an ortho position.

In another embodiment $R_1$ is —CO$_2$R$_4$; n is 0; $R_3$ is —C(O)NHR$_5$; $R_5$ is

p is 2; each $R_6$ is independently halo; and one $R_6$ is in the ortho position and the other $R_6$ is in a meta position.

In another embodiment, $R_1$ is —C(O)R$_5$.

In another embodiment $R_1$ is —C(O)R$_5$; n is 0; and $R_3$ is -halo.

In another embodiment $R_1$ is —C(O)$R_5$; n is 0; and $R_3$ is —C(O)$R_5$,

In another embodiment $R_1$ is —C(O)$R_5$; n is 0; and $R_3$ is —C(O)NHC(O)$R_5$, In another embodiment $R_1$ is —C(O)$R_5$; n is 0; and $R_3$ is —H.

In another embodiment $R_1$ is —C(O)$R_5$; n is 0; and $R_3$ is —CO$_2$(CH$_2$)$_m$($R_5$).

In another embodiment $R_1$ is —C(O)$R_5$; n is 0; and $R_3$ is —NHC(O)N($R_5$)($R_5$).

In another embodiment $R_1$ is —C(O)$R_5$; n is 0; and $R_3$ is C(O)N($R_5$)($R_5$).

In another embodiment $R_1$ is —C(O)$R_5$; n is 0; and $R_3$ is —C(O)NH$R_5$.

In another embodiment $R_1$ is —C(O)$R_5$; n is 0; $R_3$ is —C(O)NH$R_5$; and $R_5$ is

and p is an integer from 1 to 3.

In another embodiment $R_1$ is —C(O)$R_5$; n is 0; $R_3$ is —C(O)NH$R_5$; $R_5$ is

and p is 1 or 2.

In another embodiment $R_1$ is —C(O)$R_5$; n is 0; $R_3$ is —C(O)NH$R_5$; $R_5$ is

p is 1; and $R_6$ is halo and is in the para position.

In another embodiment $R_1$ is —C(O)$R_5$; n is 0; $R_3$ is —C(O)NH$R_5$; $R_5$ is

p is 1; and $R_6$ is halo and is in a meta position.

In another embodiment $R_1$ is —C(O)$R_5$; n is 0; $R_3$ is —C(O)NH$R_5$; $R_5$ is

p is 1; and $R_6$ is halo and is in an ortho position.

In another embodiment $R_1$ is —C(O)$R_5$; n is 0; $R_3$ is —C(O)NH$R_5$; $R_5$ is

p is 2; and each $R_6$ is independently -halo.

In another embodiment $R_1$ is —C(O)$R_5$; n is 0; $R_3$ is —C(O)NH$R_5$; $R_5$ is

p is 2; each $R_6$ is independently -halo; and one $R_6$ is in the para position and the other $R_6$ is in a meta position.

In another embodiment $R_1$ is —C(O)$R_5$; n is 0; $R_3$ is —C(O)NH$R_5$; $R_5$ is

p is 2; each $R_6$ is independently -halo; and one $R_6$ is in the para position and the other $R_6$ is in an ortho position.

In another embodiment $R_1$ is —C(O)$R_5$; n is 0; $R_3$ is —C(O)NH$R_5$; $R_5$ is

p is 2; and one $R_6$ is in an ortho position and the other $R_6$ is in a meta position.

In another embodiment, $R_1$ is —C(O)N$R_5R_5$.

In another embodiment $R_1$ is —C(O)N$R_5R_5$; n is 0; and $R_3$ is -halo.

In another embodiment $R_1$ is —C(O)N$R_5R_5$; n is 0; and $R_3$ is —C(O)$R_5$.

In another embodiment $R_1$ is —C(O)N$R_5R_5$; n is 0; and $R_3$ is —C(O)NHC(O)$R_5$.

In another embodiment $R_1$ is —C(O)N$R_5R_5$; n is 0; and $R_3$ is —H.

In another embodiment $R_1$ is —C(O)N$R_5R_5$; n is 0; and $R_3$ is —CO$_2$(CH$_2$)$_m$($R_5$).

In another embodiment $R_1$ is —C(O)N$R_5R_5$; n is 0; and $R_3$ is —NHC(O)N($R_5$)($R_5$).

In another embodiment $R_1$ is —C(O)NR$_5$R$_5$; n is 0; and $R_3$ is —C(O)N(R$_5$)(R$_5$).

In another embodiment $R_1$ is —C(O)NR$_5$R$_5$; n is 0; and $R_3$ is —C(O)NHR$_5$.

In another embodiment $R_1$ is —C(O)NR$_5$R$_5$; n is 0; $R_3$ is —C(O)NHR$_5$; and $R_5$ is

In another embodiment $R_1$ is —C(O)NR$_5$R$_5$; n is 0; $R_3$ is —C(O)NHR$_5$; $R_5$ is

and p is an integer from 1 to 3.

In another embodiment $R_1$ is —C(O)NR$_5$R$_5$; n is 0; $R_3$ is —C(O)NHR$_5$; $R_5$ is

and p is 1 or 2.

In another embodiment $R_1$ is —C(O)NR$_5$R$_5$; n is 0; $R_3$ is —C(O)NHR$_5$; $R_5$ is

p is 1; and $R_6$ is halo and is in the para position.

In another embodiment $R_1$ is —C(O)NR$_5$R$_5$; n is 0; $R_3$ is —C(O)NHR$_5$; $R_5$ is

p is 1; and $R_6$ is halo and is in a meta position.

In another embodiment $R_1$ is —C(O)NR$_5$R$_5$; n is 0; $R_3$ is —C(O)NHR$_5$; $R_5$ is

p is 1; and $R_6$ is halo and is in an ortho position.

In another embodiment $R_1$ is —C(O)NR$_5$R$_5$; n is 0; $R_3$ is —C(O)NHR$_5$; $R_5$ is

p is 2; and each $R_6$ is independently -halo.

In another embodiment $R_1$ is —C(O)NR$_5$R$_5$; n is 0; $R_3$ is —C(O)NHR$_5$; $R_5$ is

p is 2; each $R_6$ is independently -halo; and one $R_6$ is in the para position and the other $R_6$ is in a meta position.

In another embodiment $R_1$ is —C(O)NR$_5$R$_5$; n is 0; $R_3$ is —C(O)NHR$_5$; $R_5$ is

p is 2; each $R_6$ is independently -halo; and one $R_6$ is in the para position and the other $R_6$ is in an ortho position.

In another embodiment $R_1$ is —C(O)NR$_5$R$_5$; n is 0; $R_3$ is —C(O)NHR$_5$; $R_5$ is

p is 2; and one $R_6$ is in an ortho position and the other $R_6$ is in a meta position.

In another embodiment, the compounds of formula (Ic) are the compounds of formula (Ia) and pharmaceutically acceptable salts and hydrates thereof, above.

In another embodiment, the compounds of formula (Ic) are the compounds of formula (Ib) and pharmaceutically acceptable salts and hydrates thereof, above.

Illustrative compounds of formula (Ic) are:

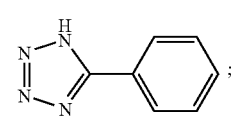

Compound FF

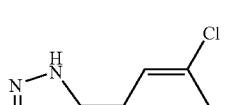

Compound FG

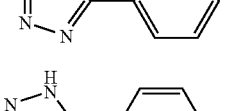

Compound FH

-continued
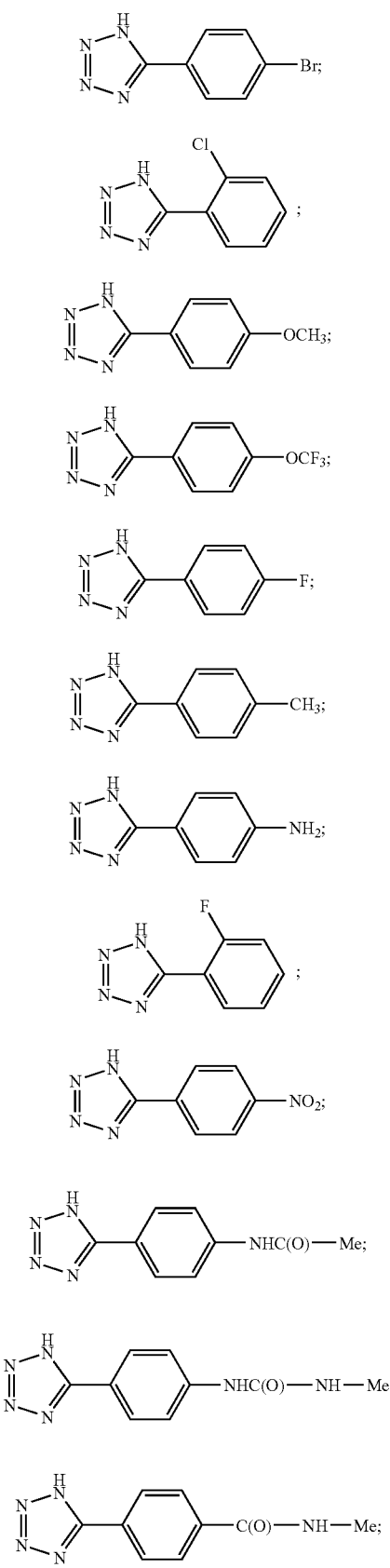
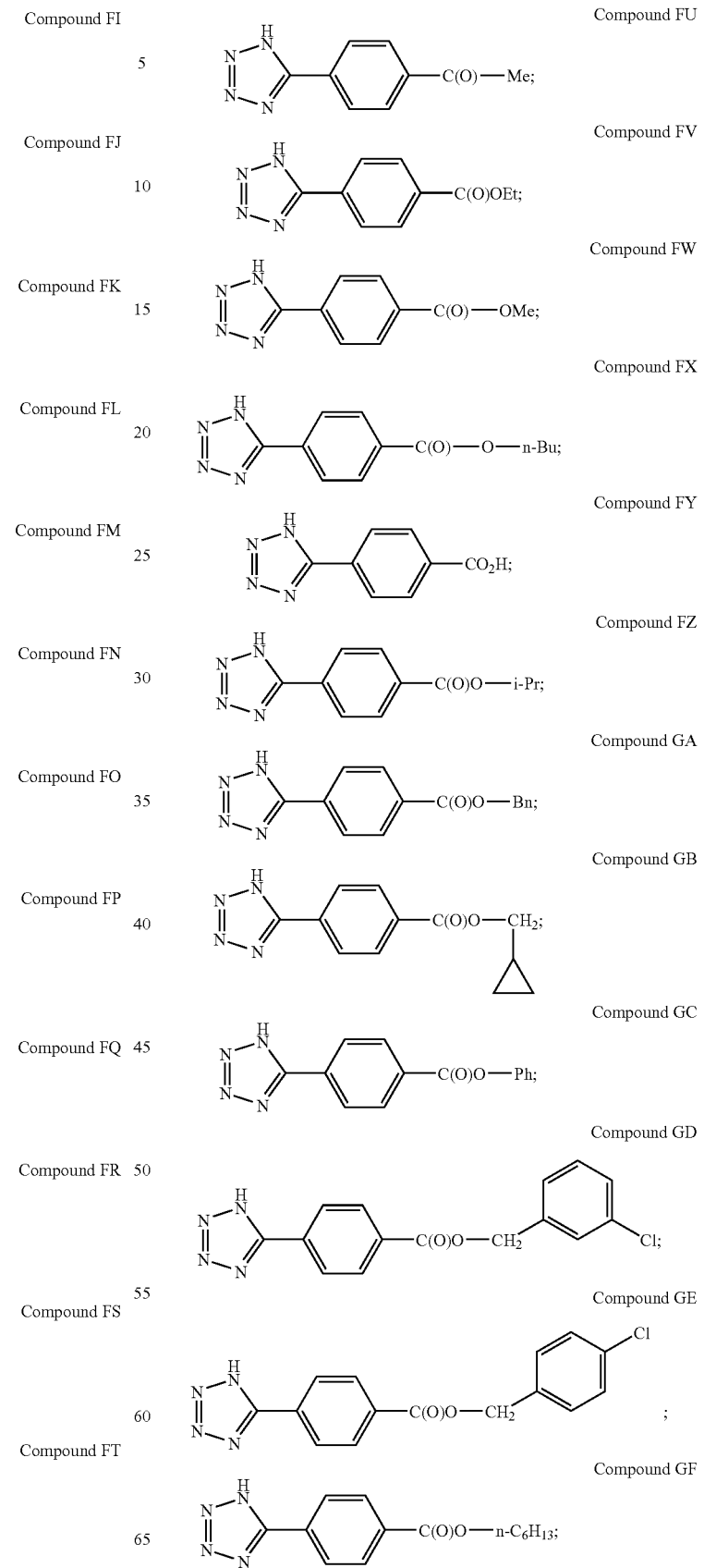

-continued

Compound GG: 5-(4-(C(O)O-n-C8H15)phenyl)-1H-tetrazole

Compound GH: 5-(4-(C(O)O-cyclohexyl)phenyl)-1H-tetrazole

Compound GI: 5-(4-(C(O)OCH2-adamantyl)phenyl)-1H-tetrazole

Compound GJ: 5-(4-(C(O)OCH2CF3)phenyl)-1H-tetrazole

Compound GK: 5-(4-(C(O)OCH2CH2-morpholino)phenyl)-1H-tetrazole

Compound GL: 5-(4-(C(O)OCH2CH2-pyrrolidino)phenyl)-1H-tetrazole

Compound GM: tetrazolyl-phenyl-C(O)O-CH2CH2CH2-C≡CH

Compound GN: tetrazolyl-phenyl-C(O)O-(pyridine N-oxide)

Compound GO: tetrazolyl-phenyl-C(O)O-cyclohexyl

Compound GP: tetrazolyl-phenyl-C(O)O-CH2CF2CF2H

Compound GQ: tetrazolyl-phenyl-C(O)O-CH2-C≡C-CH2-CH3

Compound GR: tetrazolyl-phenyl-C(O)O-CH2-(cyclohexenyl with isopropenyl substituent)

Compound GS: tetrazolyl-phenyl-C(O)O-CH2CH(CF3)CH2CF3

Compound GT: tetrazolyl-phenyl-C(O)O-(3-bromophenyl)

Compound GU: tetrazolyl-phenyl-C(O)O-CH2-(4-bromophenyl)

Compound GV: tetrazolyl-phenyl-C(O)O-CH2CCl3

Compound GW: tetrazolyl-phenyl-C(O)O-CH2CH2-(succinimidyl)

Compound GX: tetrazolyl-phenyl-C(O)O-CH2-(2-iodophenyl)

Compound GY: tetrazolyl-phenyl-C(O)O-(decahydronaphthalen-2-yl)

-continued

Compound GZ, Compound HA, Compound HB, Compound HC, Compound HD, Compound HE, Compound HF, Compound HG, Compound HH, Compound HI, Compound HJ, Compound HK, Compound HL, Compound HM, Compound HN, Compound HO, Compound HP, Compound HQ, Compound HR

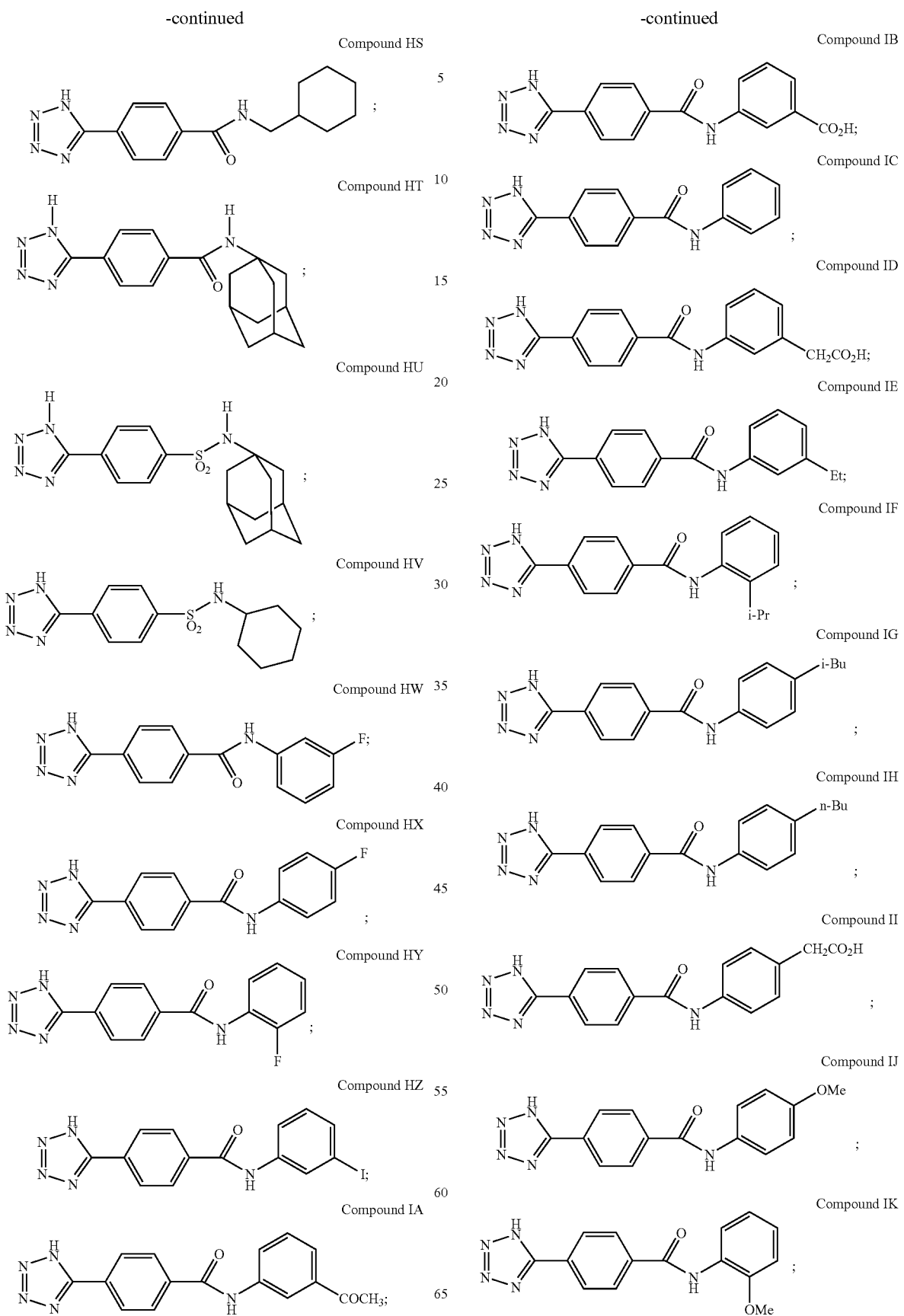

-continued
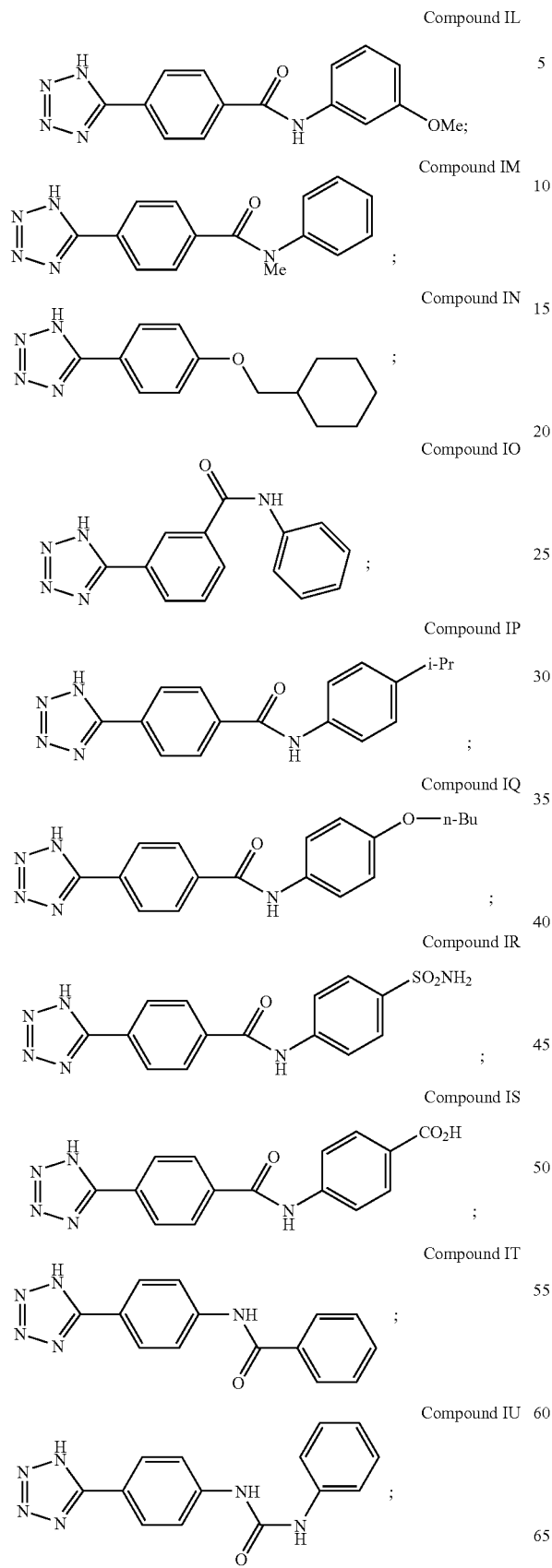
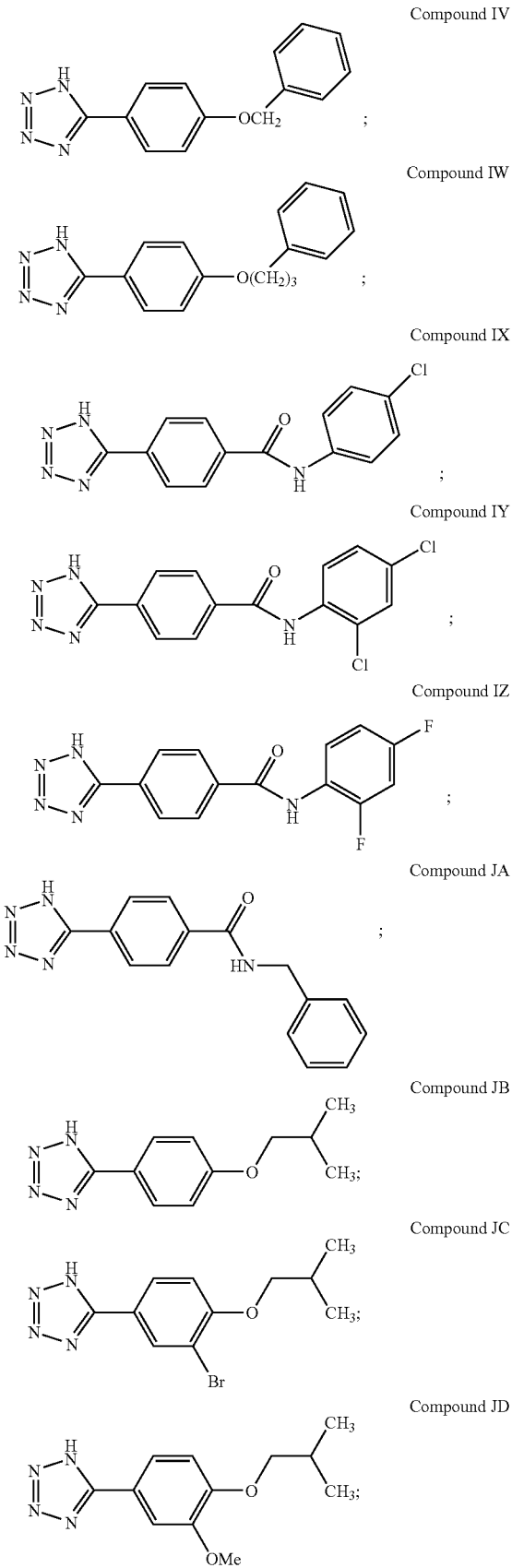

-continued

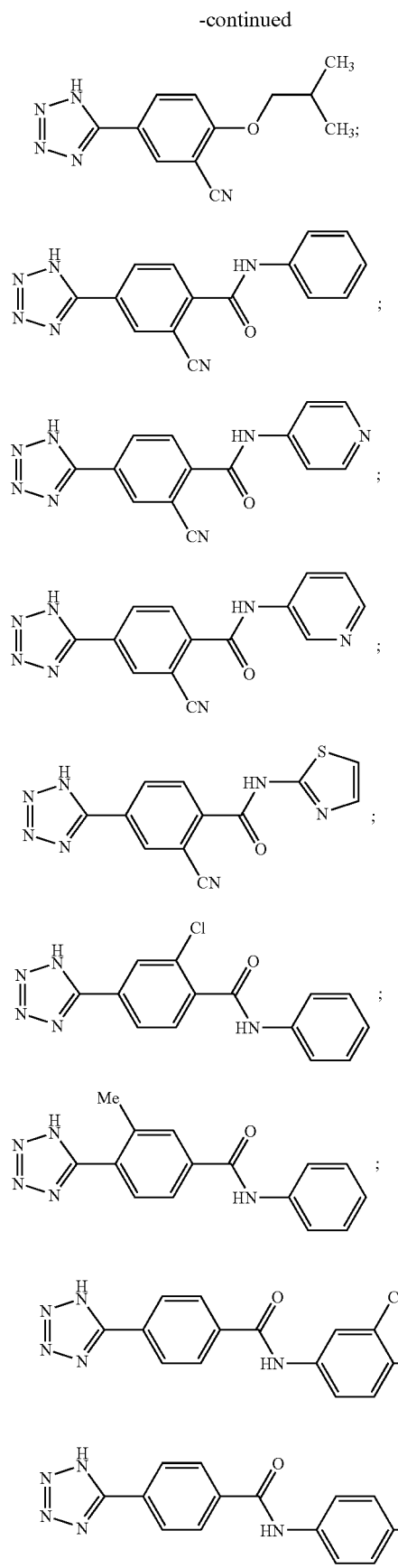

Compound JE

Compound JF

Compound JG

Compound JH

Compound JI

Compound JJ

Compound JK

Compound JL

Compound JM

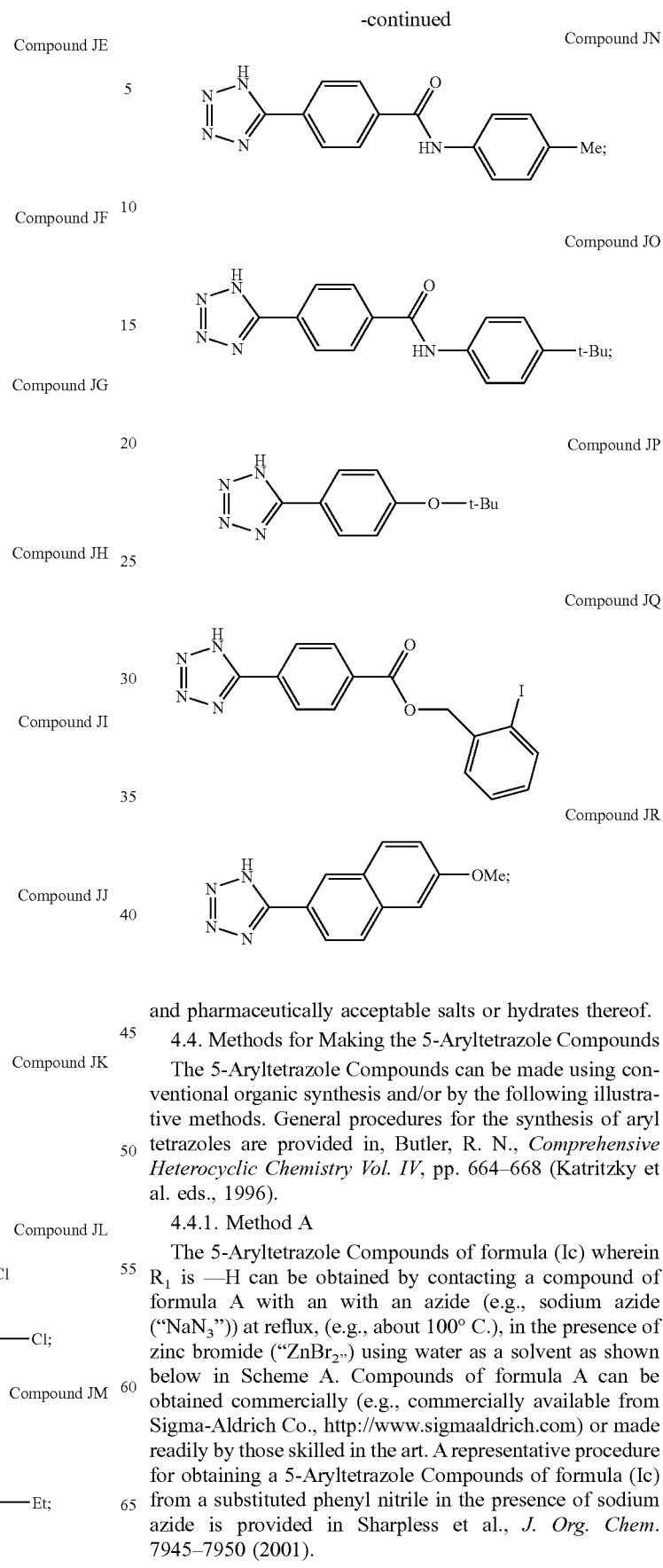

Compound JN

Compound JO

Compound JP

Compound JQ

Compound JR and pharmaceutically acceptable salts or hydrates thereof.

4.4. Methods for Making the 5-Aryltetrazole Compounds

The 5-Aryltetrazole Compounds can be made using conventional organic synthesis and/or by the following illustrative methods. General procedures for the synthesis of aryl tetrazoles are provided in, Butler, R. N., *Comprehensive Heterocyclic Chemistry Vol. IV*, pp. 664–668 (Katritzky et al. eds., 1996).

4.4.1. Method A

The 5-Aryltetrazole Compounds of formula (Ic) wherein $R_1$ is —H can be obtained by contacting a compound of formula A with an with an azide (e.g., sodium azide ("NaN$_3$")) at reflux, (e.g., about 100° C.), in the presence of zinc bromide ("ZnBr$_2$") using water as a solvent as shown below in Scheme A. Compounds of formula A can be obtained commercially (e.g., commercially available from Sigma-Aldrich Co., http://www.sigmaaldrich.com) or made readily by those skilled in the art. A representative procedure for obtaining a 5-Aryltetrazole Compounds of formula (Ic) from a substituted phenyl nitrile in the presence of sodium azide is provided in Sharpless et al., *J. Org. Chem.* 7945–7950 (2001).

Scheme A

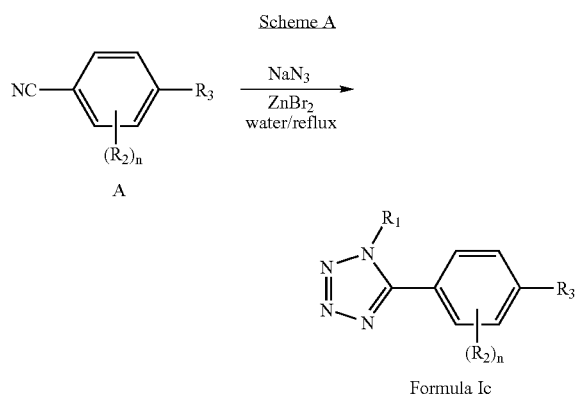

Formula Ic

A 5-Aryltetrazole Compound of formula (Ic) wherein $R_1$ is —$CO_2R_4$, —$C(O)R_5$, or —$C(O)N(R_5)(R_5)$ can be obtained by contacting a 5-Aryltetrazole Compound of formula (Ic), wherein $R_1$ is —H with an acyl compound (e.g., $XCO_2R_4$, $XC(O)R_5$, or $XC(O)N(R_5)(R_5)$, wherein X is Br or Cl) in triethylamine ($NEt_3$).

4.4.2. Method B

In another embodiment, a 5-Aryltetrazole Compounds of formula (Ic) wherein $R_1$ is H can be obtained by contacting a compound of formula A with an azide, (e.g., azidotrimethylsilane ("TMSN$_3$")) and a catalytic amount of dibutyl tin oxide ("n-Bu$_2$SnO") in refluxing toluene as a solvent as shown below in Scheme B. Methods for obtaining tetrazoles from nitriles and TMSN$_3$ are provided in, for example, Curran et al., *Tetrahedron*, 1999, 55, 8997–9006.

Scheme B

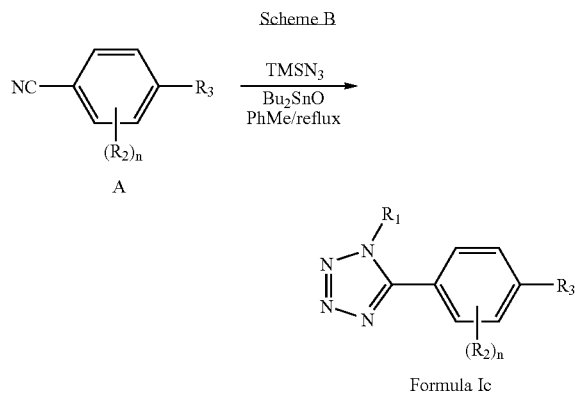

Formula Ic

A 5-Aryltetrazole Compound of formula (Ic) wherein $R_1$ is —$CO_2R_4$, —$C(O)R_5$, or —$C(O)N(R_5)(R_5)$ can be obtained by contacting a 5-Aryltetrazole Compound of formula (Ic), wherein $R_1$ is —H with an acyl compound (e.g., $XCO_2R_4$, $XC(O)R_5$, or $XC(O)N(R_5)(R_5)$, wherein X is Br or Cl) in triethylamine ($NEt_3$). Where $R_5$ is —H, protecting group chemistry can be used.

4.4.3. Method C

The 5-Aryltetrazole Compounds of formula (Ic) wherein $R_1$ is —H can be converted to 5-Aryltetrazole compounds of formula (Ia) by contacting the compound of formula (Ic) wherein $R_1$ is —H with an alkyl chlorocarbonate or carbonic acid anhydride under conditions suitable for the formation of a carbamate as shown in Scheme C. Methods for obtaining carbamates from amines and carbonates are provided in, for example, Raucher et al., *Synthetic Commun.* 1985, 15, 1025. For example, illustrative compounds AA-AZ, BA-BZ, CA-CZ, DA-DZ, EA-EG can be made using this method.

Scheme C

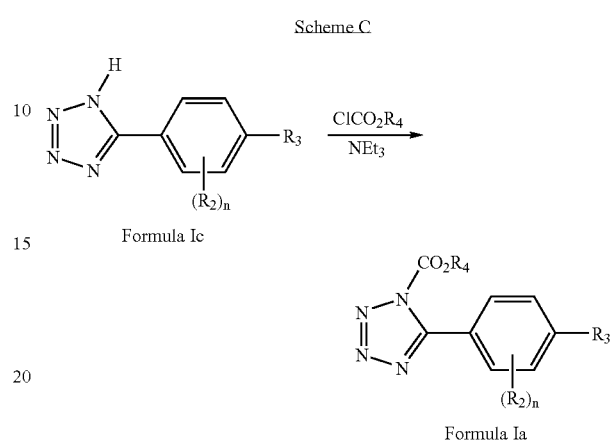

Formula Ia 4.4.4. Method D

In another embodiment, a 5-Aryltetrazole Compound of formula (Ib) wherein $R_1$ is —H can be obtained by contacting a compound of formula B with a 4-substituted aniline (e.g., 4-methylaniline or 4-methoxyaniline) to obtain a compound of formula D'. The compound of formula D' is then contacted with azide, (e.g., azidotrimethylsilane ("TMSN$_3$")) and a catalytic amount of dibutyl tin oxide ("n-Bu$_2$SnO") in refluxing toluene as a solvent as shown below in Scheme B. Methods for obtaining tetrazoles from nitriles and TMSN$_3$ are provided in, for example, Curran et al. (see, e.g., section 4.4.2, above).

Scheme D

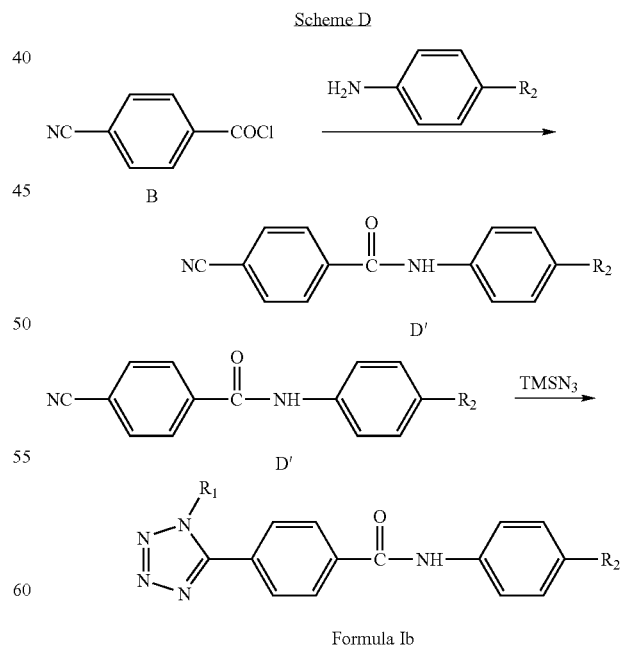

Formula Ib

To obtain a 5-Aryltetrazole Compound of formula (Ib) wherein $R_1$ is —$CO_2R_4$, —$C(O)R_5$, or —$C(O)N(R_5)(R_5)$, a 5-Aryltetrazole Compound of formula (Ib) wherein $R_1$ is —H is contacted with an acyl derivative (e.g., $XCO_2R_4$, $XC(O)R_5$, or $XC(O)N(R_5)(R_5)$, wherein X is Br or Cl) in triethylamine ($NEt_3$) to provide a 5-Aryltetrazole Compound of formula (Ib). Where $R_5$ is —H, protecting group chemistry can be used. For example, illustrative compounds EH-FE can be made using this method.

5-Aryltetrazole Compounds can have asymmetric centers and therefore can exist in particular enantiomeric and/or diastereomeric forms. A 5-Aryltetrazole Compound can be in the form of an optical isomer or a diastereomer. Accordingly, the invention encompasses 5-Aryltetrazole Compounds and their uses as described herein in the form of their optical isomers, diastereomers, and mixtures thereof, including a racemic mixture.

In addition, one or more hydrogen, carbon or other atoms of a 5-Aryltetrazole Compound can be replaced by an isotope of the hydrogen, carbon, or other atom. Such compounds, which are encompassed by the present invention, are useful as research and diagnostic tools in metabolism pharmokinetic studies and binding assays.

4.5. Prophylactic and/or Therapeutic Uses of the 5-Aryltetrazole Compounds

In accordance with the invention, an effective amount of a 5-Aryltetrazole Compound, or a pharmaceutical composition comprising an effective amount of a 5-Aryltetrazole Compound, is administered to an animal in need of treatment or prevention of an inflammation disease, a reperfusion disease, or hyperuricemia. In one embodiment, an effective amount of a 5-Aryltetrazole Compound can be used to treat or prevent any condition that is treatable or preventable by inhibiting xanthine oxidase. Examples of cells that express xanthine oxidase include, but are not limited to, lung, liver, and intestinal cells.

Examples of conditions that are treatable or preventable by inhibiting xanthine oxidase include, but are not limited to, an inflammation disease, a reperfusion disease, or hyperuricemia. In another embodiment, an effective amount of a 5-Aryltetrazole Compound can be used to treat or prevent an inflammation disease, a reperfusion disease, or hyperuricemia.

Examples of inflammation diseases include, but are not limited to, chronic inflammatory disorders of the joints including arthritis, e.g., rheumatoid arthritis and osteoarthritis; respiratory distress syndrome; inflammatory bowel disorders; and inflammatory lung disorders such as asthma and chronic obstructive airway disease, inflammatory disorders of the eye such as corneal dystrophy, trachoma, onchocerciasis, uveitis, sympathetic ophthalmitis, and endophthalmitis; inflammatory disorders of the gum, e.g., periodontitis and gingivitis; tuberculosis; leprosy; inflammatory diseases of the kidney including glomerulonephritis and nephrosis; inflammatory disorders of the skin including acne, sclerodermatitis, psoriasis, eczema, photoaging and wrinkles; inflammatory diseases of the central nervous system, including AIDS-related neurodegeneration, stroke, neurotrauma, Alzheimer's disease, encephalomyelitis and viral or autoimmune encephalitis; autoimmune diseases including immune-complex vasculitis, systemic lupus and erythematodes; systemic lupus erythematosus (SLE); and inflammatory diseases of the heart such as cardiomyopathy.

Examples of inflammatory bowel disorders include, but are not limited to, ileitis, including, but not limited to, regional ileitis; colitis, including, but not limited to, ulcerative colitis, collagenous/microscopic colitis, and enterocolitis; Crohn's disease; and pouchitis.

Examples of reperfusion diseases include, but are not limited to, shock and sepsis. Shock can be septic shock, e.g., gram positive bacteria-mediated circulatory shock, gram negative bacteria-mediated circulatory shock, hemorrhagic shock, anaphylactic shock, shock associated with systemic inflammation, shock associated with pro-inflammatory cytokines, and shock associated with systemic inflammatory response syndrome (SIRS). The 5-Aryltetrazole Compounds can also be used to prevent or treat circulatory shock, such as shock occurring as a result of gram negative and gram positive sepsis, trauma, hemorrhage, burn injury, anaphylaxis, cytokine immunotherapy, organ failure (particularly kidney or liver failure), or systemic inflammatory response syndrome. Other examples of reperfusion disease are disease arising from cell or solid-organ transplantation, cardiopulmonary bypass surgery, compartment syndrome, crush injury, splanchnic ischemia-reperfusion, myocardial infarction and stroke.

Examples of hyperuricemia include, but are not limited to, gout; tumor-lysis syndrome; idiopathic hyperuricemia; hyperuricemia inherited including, but not limited to, hyperuricemia due to PP-ribose-P synthetase overactivity; hypoxanthine-gaunine phosphoribosyltransferase deficiency; glucose-6-phosphate deficiency; Gierke's glycogen storage disease; chronic hemolytic hyperuricemia including, but not limited to, erythroid, myeloid, and lymphoid proliferative hyperuricemia; renal mechanistic hyperuricemia including, but not limited to, familial progressive renal insufficiency, acquired chronic renal insufficiency, drug related renal insufficiency, and endogenous renal production disorders.

Examples of tumor-lysis syndrome include, but are not limited to, tumor-lysis syndrome resulting from chemotherapy treatment in patients with cancer, including but not limited to, leukemias, lymphomas, small cell lung cancer, and breast cancer. In one embodiment, the tumor-lysis syndrome is that which results from chemotherapy, particularly for treating cancer.

4.6. Methods for Administration

Due to their activity, the 5-Aryltetrazole Compounds are advantageously useful in veterinary and human medicine. As described above, the 5-Aryltetrazole Compounds are useful for treating or preventing an inflammation disease, a reperfusion disease, or hyperuricemia.

When administered to an animal, an effective amount of a 5-Aryltetrazole Compound can be administered as a component of a composition that comprises a pharmaceutically acceptable carrier or vehicle. The present compositions, which comprise a 5-Aryltetrazole Compound, are in one embodiment administered orally. The compositions of the invention can also be administered by any other convenient route, for example, by infusion or bolus injection, by absorption through epithelial or mucocutaneous linings (e.g., oral mucosa, rectal, and intestinal mucosa, etc.) and may be administered together with another therapeutic agent. Administration can be systemic or local. Various delivery systems are known, e.g., encapsulation in liposomes, microparticles, microcapsules, capsules, etc., and can be used to administer the 5-Aryltetrazole Compounds.

Methods of administration include, but are not limited to, intradermal, intramuscular, intraperitoneal, intravenous, subcutaneous, intranasal, epidural, oral, sublingual, intracerebral, intravaginal, transdermal, rectally, by inhalation, or topically, particularly to the ears, nose, eyes, or skin. The mode of administration is left to the discretion of the practitioner. In most instances, administration will result in the release of the 5-Aryltetrazole Compounds into the bloodstream.

In specific embodiments, it may be desirable to administer the 5-Aryltetrazole Compounds locally. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

In certain embodiments, it may be desirable to introduce the 5-Aryltetrazole Compounds into the central nervous system by any suitable route, including intraventricular, intrathecal, and epidural injection. Intraventricular injection may be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the 5-Aryltetrazole Compounds can be formulated as a suppository, with traditional binders and excipients such as triglycerides.

In another embodiment, the 5-Aryltetrazole Compounds can be delivered in a vesicle, in particular a liposome (see Langer, *Science* 249:1527–1533 (1990) and Treat et al., *Liposomes in the Therapy of Infectious Disease and Cancer* 317–327 and 353–365 (1989).

In yet another embodiment, the 5-Aryltetrazole Compounds can be delivered in a controlled-release system (see, e.g., Goodson, in Medical Applications of Controlled Release, supra, vol. 2, pp. 115–138 (1984)). Other controlled-release systems discussed in the review by Langer, *Science* 249:1527–1533 (1990) may be used. In one embodiment, a pump may be used (Langer, *Science* 249:1527–1533 (1990); Sefton, *CRC Crit. Ref. Biomed. Eng.* 14:201 (1987); Buchwald et al., *Surgery* 88:507 (1980); and Saudek et al., *N. Engl. J. Med.* 321:574 (1989)). In another embodiment, polymeric materials can be used (see *Medical Applications of Controlled Release* (Langer and Wise eds., 1974); *Controlled Drug Bioavailability, Drug Product Design and Performance* (Smolen and Ball eds., 1984); Ranger and Peppas, *J. Macromol. Sci. Rev. Macromol. Chem.* 23:61 (1983); Levy et al., *Science* 228:190 (1985); During et al., *Ann. Neurol.* 25:351 (1989); and Howard et al., *J. Neurosurg.* 71:105 (1989)). In yet another embodiment, a controlled-release system can be placed in proximity of a target of the 5-Aryltetrazole Compound, e.g., the spinal column or brain, thus requiring only a fraction of the systemic dose.

The present compositions can optionally comprise a suitable amount of a pharmaceutically acceptable carrier or vehicle so as to provide the form for proper administration to the animal.

Such pharmaceutical carriers or vehicles can be liquids, such as water and oils, including those of petroleum, animal, vegetable, or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating, and coloring agents may be used. When administered to an animal, the pharmaceutically acceptable carriers or vehicle s are preferably sterile. Water is a particularly useful vehicle when the 5-Aryltetrazole Compound of the invention is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the composition is in the form of a capsule (see e.g., U.S. Pat. No. 5,698,155). Other examples of suitable pharmaceutical excipients are described in *Remington's Pharmaceutical Sciences* 1447–1676 (Alfonso R. Gennaro ed., 19th ed. 1995), incorporated herein by reference.

In one embodiment, the 5-Aryltetrazole Compounds are formulated in accordance with routine procedures as a composition adapted for oral administration to human beings. Compositions for oral delivery may be in the form of tablets, lozenges, aqueous or oily suspensions, granules, powders, emulsions, capsules, syrups, or elixirs, for example. Orally administered compositions may contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard excipients such as mannitol, lactose, starch, magnesium stearate, sodium saccharin, cellulose and magnesium carbonate. Such excipients are preferably of pharmaceutical grade.

In another embodiment, the 5-Aryltetrazole Compounds can be formulated for intravenous administration. Typically, compositions for intravenous administration comprise sterile isotonic aqueous buffer. Where necessary, the compositions may also include a solubilizing agent. Compositions for intravenous administration may optionally include a local anesthetic such as lignocaine to lessen pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the 5-Aryltetrazole Compounds are to be administered by infusion, they can be dispensed, for example, with an infusion bottle containing sterile pharmaceutical grade water or saline. Where the 5-Aryltetrazole Compounds are administered by injection, an ampoule of sterile water for injection or saline can be provided so that the ingredients may be mixed prior to administration.

The 5-Aryltetrazole Compounds of the invention can be administered by controlled-release means or by delivery devices that are well known to those of ordinary skill in the art. Examples include, but are not limited to, those described in U.S. Pat. Nos.: 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

The amount of the 5-Aryltetrazole Compound that is effective in the treatment or prevention of an inflammation disease, a reperfusion disease, or hyperuricemia and/or for inhibiting xanthine oxidase activity can depend on the nature of the disorder or condition causing the inflammation disease, reperfusion disease, or hyperuricemia, or the need for inhibiting xanthine oxidase activity and can be determined by standard clinical techniques. In addition, in vitro or in vivo assays may optionally be employed to help identify dosage ranges. The effective amount to be employed will also depend on the route of administration, and the seriousness of the inflammation disease, reperfusion disease, or hyperuricemia and/or need for inhibiting xanthine oxidase activity and can be decided according to the judgment of the practitioner and each patient's circumstances. Administration can be at an effective amount ranging from about 0.1 to about 500 mg/kg/day of the 5-Aryltetrazole Compound to animal in need thereof. Suitable effective amounts can range from about 0.1 milligrams to about 500 milligrams about every 4 h, although typically about 100 mg or less. In one embodiment the effective amounts range from about 0.01 milligrams to about 500 milligrams of a 5-Aryltetrazole Compound about every 4 h, in another embodiment about 0.020 milligrams to about 50 milligrams about every 4 h, and in another embodiment about 0.025 milligrams to about 20 milligrams about every 4 h. The effective amounts described herein refer to total amounts administered; that is, if more than one 5-Aryltetrazole Compound is administered, the effective amounts correspond to the total amount administered.

The 5-Aryltetrazole Compounds can be assayed in vitro or in vivo, for the desired therapeutic or prophylactic activity, prior to use in humans. Animal model systems can be used to demonstrate safety and efficacy.

The present methods for treating or preventing inflammation disease, a reperfusion disease, or hyperuricemia in an animal in need thereof can further comprise administering to the animal being administered a 5-Aryltetrazole Compound an effective amount of another therapeutic agent.

Effective amounts of the other therapeutic agents are well known to those skilled in the art. However, it is well within the skilled artisan's purview to determine the other therapeutic agent's optimal effective-amount range. In one embodiment of the invention where another therapeutic agent is administered to an animal, the effective amount of the 5-Aryltetrazole Compound is less than its effective amount would be where the other therapeutic agent is not administered. In another embodiment, the 5-Aryltetrazole Compound and the other therapeutic agent act synergistically to treat an inflammation disease, a reperfusion disease, or hyperuricemia. It is to be understood that where the methods comprise administering an effecitve amount of a 5-Aryltetrazole Compound and another therapeutic agent, the 5-Aryltetrazole Compound is adminstered when the other therapeutic agent exerts its therapeutic effect, or the other therapeutic agent is administered when the 5-Aryltetrazole Compound exerts its therapeutic or prophylactic effect.

The other therapeutic agent can be a non-steroidal anti-inflammatory agent. Useful non-steroidal anti-inflammatory agents, include, but are not limited to, aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam; salicylic acid derivatives, including aspirin, sodium salicylate, choline magnesium trisalicylate, salsalate, diflunisal, salicylsalicylic acid, sulfasalazine, and olsalazin; para-aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid, and meclofenamic acid; enolic acids, including oxicams (piroxicam, tenoxicam), and pyrazolidinediones (phenylbutazone, oxyphenthartazone); and alkanones, including nabumetone and pharmaceutically acceptable salts thereof and mixtures thereof. For a more detailed description of the NSAIDs, see Paul A. Insel, *Analgesic-Antipyretic and Antiinflammatory Agents and Drugs Employed in the Treatment of Gout*, in Goodman & Gilman's *The Pharmacological Basis of Therapeutics* 617–57 (Perry B. Molinhoff and Raymond W. Ruddon eds., 9$^{th}$ ed 1996) and Glen R. Hanson, *Analgesic, Antipyretic and Anti-Inflammatory Drugs in Remington: The Science and Practice of Pharmacy Vol II* 1196–1221 (A. R. Gennaro ed. 19th ed. 1995) which are hereby incorporated by reference in their entireties.

The other therapeutic agent can be an anticonvulsant. Useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenytoin, mephobarbital, metharbital, methetoin, methsuximide, 5-methyl-5-(3-phenanthryl)-hydantoin, 3-methyl-5-phenylhydantoin, narcobarbital, nimetazepam, nitrazepam, oxcarbazepine, paramethadione, phenacemide, phenetharbital, pheneturide, phenobarbital, phensuximide, phenylmethylbarbituric acid, phenytoin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, and zonisamide.

The other therapeutic agent can be an anti-depressant. Useful antidepressants include, but are not limited to, binedaline, caroxazone, citalopram, dimethazan, fencamine, indalpine, indeloxazine hydrocholoride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

The other therapeutic agent can be an anti-hyperuricemic agent. Useful anti-hyperuricemic agents also include, but are not limited to, allopurinol.

The other therapeutic agent can be an agent useful in treating or preventing tumor-lysis syndrome. Therapeutic agents useful for treating or preventing tumor-lysis syndrome also include, but are not limited to, Lasix or Zyloprim.

The other therapeutic agent can be an agent useful in treating or preventing an inflammatory bowel disorder. Therapeutic agents useful for treating or preventing an inflammatory bowel disorder include, but are not limited to, sulfasalazine, olsalazine, and mesalamine.

A 5-Aryltetrazole Compound and the other therapeutic agent can act additively or, more preferably, synergistically. In one embodiment, a 5-Aryltetrazole Compound is administered concurrently with another therapeutic agent. In one embodiment, a composition comprising an effective amount of a 5-Aryltetrazole Compound and an effective amount of another therapeutic agent can be administered. Alternatively, a composition comprising an effective amount of a 5-Aryltetrazole Compound and a different composition comprising an effective amount of another therapeutic agent can be concurrently administered. In another embodiment, an effective amount of a 5-Aryltetrazole Compound is administered prior or subsequent to administration of an effective amount of another therapeutic agent.

4.7. Kits

The invention encompasses kits that can simplify the administration of a 5-Aryltetrazole Compound to an animal.

A typical kit of the invention comprises a unit dosage form of a 5-Aryltetrazole Compound. In one embodiment, the unit dosage form is a container, which can be sterile, containing an effective amount of a 5-Aryltetrazole Compound and a pharmaceutically acceptable carrier or excipient. The kit can further comprise a label or printed instructions instructing the use of the 5-Aryltetrazole Compound to treat or prevent inflammation disease, reperfusion disease, or hyperuricemia. The kit can also further comprise a unit dosage form of another therapeutic agent, for example, a container containing an effective amount of the other therapeutic agent. In one embodiment, the kit comprises a container containing an effective amount of a 5-Aryltetrazole Compound and an effective amount of another therapeutic agent. Examples of other therapeutic agents include, but are not limited to, those listed above.

Kits of the invention can further comprise devices that are useful for administering the unit dosage forms. Examples of such devices include, but are not limited to, syringes, drip bags, patches, enema bags, and inhalers.

The following examples are set forth to assist in understanding the invention and should not, of course, be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

5. EXAMPLES 5.1. Example 1

Synthesis of Compound IC

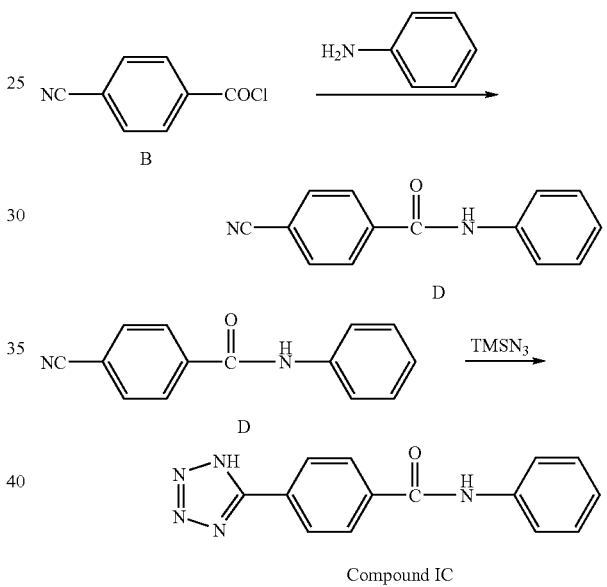

Compound IC

A solution of 4-cyanobenzoylchloride B (0.82 g, 5 mmol) (commercially available from Sigma-Aldrich Co., http://www.sigmaaldrich.com) was stirred in dry toluene (20 mL). Aniline (0.5 mL, 0.55 mmol) was added dropwise, and following the initial exothermic reaction, the suspension was refluxed for 2 h. After cooling to room temperature, hexane (100 mL) was added to the reaction mixture and the precipitate was filtered and washed with hexane to afford Compound D: Yield 2.0 g (90%), $^1$H NMR (DMSO-D$_6$): δ 7.1 (t, 1H, p-H—NHPh) 7.35 (t, 2H, m-H, NHPh) , 7.75 (d, 2H, o-H, NHPh); 8.15 (AA'BB', Δ=27 Hz, 4H, C(O)Ar), 10.45 (s, 1H, C(O)NH).

A mixture of Compound D (2.2 g, 10 mmol), azidotrimethylsilane (2 mL, 15 mmol) and dibutyltin oxide (0.5 g, 2 mmol) in anhydrous toluene (40 mL) was heated at 100° C. for 5 h. The progress of the reaction was monitored by Thin-Layer Chromatography. After completion of the reaction the organic phase was extracted with 1 M NaOH (20 mL). The aqueous layer was washed with ethyl acetate (2×20 mL) and acidified to pH 2 using 2 M HCl. The separated white solid was collected by filtration to provide Compound IC: Yield 1.95 g (75%). $^1$H NMR (DMSO-D$_6$):

δ 5 7.1 (t, 1H, p-H, NHPh) 7.35 (t, 2H, m-H, NHPh), 7.8 (d, 2H, o-H, NHPh); 8.15 (AA'BB', Δ=12 Hz, 4H, C(O)Ar), 10.4 (s, 1H, C(O)NH). ES/MS: m/z⁺ 263 (M⁺+1, 100%).

5.2. Example 2

Alternative Synthesis of Compound IC

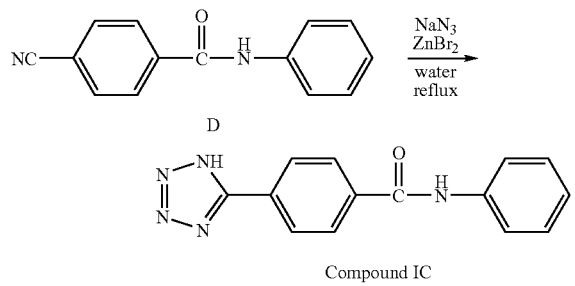

Compound IC

A mixture of Compound D (2.2 g, 10 mmol), sodium azide (1.3 g, 20 mmol), zinc bromide (1.15 g, 10 mmol) and isopropanol (5 mL) in water (20 mL) was stirred at reflux for 48 h. After the mixture was cooled to 60° C., 50 mL of 2 M NaOH was added and the suspension was stirred for additional 30 min at this temperature. The precipitate was filtered and the aqueous solution was extracted with ethyl acetate (2×50 mL). The aqueous layer was separated and acidified to pH 2 using 2 M HCl. The precipitate was filtered and washed thoroughly with water to provide Compound IC. Yield 1.3 g (50%).

Experimental data for illustrative 5-Aryltetrazoles Compounds prepared using the methods analogous to those above are given below.

5.3. Example 3

Compounds FT, HA-HC, HK, HL, HS, HT, HW-IM, IO, IP, IS, IX-JA, JG-JI, and JK-JO

Compounds FT, HA-HC, HK, HL, HS, HT, HW-IF, IH-IM, IO, IS, IX-JA, JG-JI, and JK-JN were prepared according to the method of example 1 using the corresponding amine in place of aniline. Compounds JO, IP, and IG were prepared according to the method of examples 1 and 2 using the corresponding amine in place of aniline.

Experimental data for illustrative 5-Aryltetrazoles Compounds prepared using the method in Section 5.1 are given below.

5.3.1. Compound HX: $^1$H NMR (DMSO-D$_6$): δ 7.2 (t, 2H, m-H, NHAr), 7.8 (q, 2H, o-H, NHAr), 8.05 (AA'BB', Δ=10 Hz, 4H, C(O)Ar), 10.4 (s, 1H, C(O)NH).

5.3.2. Compound IA: $^1$H NMR (DMSO-D$_6$): δ 2.6 (S, 3H, CH$_3$), 7.5 (d, 1H 3-H, NHAr), 7.7 (d, 1H, 4-H, NHAr), 8.1 (m, 5H, 2-H NAr+C(O)Ar), 8.4 (s, 1H, 6-H, NHAr), 10.6 (s, 1H, C(O)NH).

5.3.3. Compound IP: $^1$H NMR (DMSO-D$_6$): δ 1.2 (d, 6H, 2CH$_3$), 2.8 (m, 1H, CH(CH$_3$)$_2$), 7.4 (AA'BB', Δ=140 Hz, 4H, C(O)Ar), 8.05 (AA'BB', m, 4H, C(O)Ar), 10.6 (s, 1H, C(O)NH).

5.3.4. Compound IS: $^1$H NMR (DMSO-D$_6$): δ 6 7.9 (s, 4H, NHAr), 8.1 (AA'BB', Δ=34 Hz, 4H, C(O)Ar), 10.6 (s, 1H, C(O)NH).

5.3.5. Compound JN: $^1$H NMR (DMSO-D$_6$): δ 2.2 (s, 3H, CH$_3$), 7.4 (AA'BB', Δ=154 Hz, 4H, NHAr), 8.05 (AA'BB', Δ=14 Hz, 4H, C(O)Ar), 10.3 (s, 1H, C(O)NH).

5.4. Example 4

Synthesis of Compounds FV-FX, FZ-GZ, HO-HR, and JQ

Compounds FV-FX, FZ-GZ, HO-HR, AND JQ were prepared according to Method B (described in Section 4.4 above) from the corresponding esters of 4-cyanobenzoic acid. These esters were obtained from 4-cyanobenzoyl chloride and an alcohol or a halide as described in Vogel's Textbook of Practical Organic Chemistry 5th Ed., p. 695. Such alcohols and halides are commercially available.

5.5. Example 5

Synthesis of Compounds IN, IR, IV, IW, and JB-JE

To a solution of 4-cyanophenol (1.2 g, 10 mmol) in dry DMF (20 mL) was added triethylamine (20 mmol) followed by i-butyl bromide (2.7 g, 20 mmol). The resulting reaction mixture was stirred at 100° C. for 6 h. After cooling to room temperature, the reaction mixture was diluted with water (100 mL) and extracted with ethyl acetate (2×40 mL). The organic layer was washed with 4 M KOH (3×30 mL) and then with water, dried over Na$_2$SO$_4$ and concentrated under vacuum to provide 1.5 g (85%) 4-iso-butoxybenzonitrile that was used for the next step without further purification. $^1$H NMR (DMSO-D$_6$): δ 0.95 (d, 6H, 2CH$_3$), 2.0 (m, 1H, CH(CH$_3$)$_2$), 3.8 (d, 2H, CH$_2$), 7.4 (AA'BB', Δ=270 Hz, 4H, Ar).

A mixture of 4-iso-butoxybenzonitrile (1.75 g, 10 mmol), azidotrimethylsilane (2 mL, 15 mmol) and dibutyltinoxide (0.5 g, 2 mmol) in anhydrous toluene (40 mL) was heated at 100° C. for 18 h. While still hot, the organic phase was extracted with 20 mL 1 M NaOH, aqueous layer was washed with ethyl acetate (2×20 mL) and acidified to pH 2 using 2 M HCl. The resulting white solid was collected by filtration to provide Compound IR: Yield 1.2 g (55%). $^1$H NMR (DMSO-D$_6$): δ 0.95 (d, 6H, 2CH$_3$), 2.0 (m, 1H, CH(CH$_3$)$_2$), 3.8 (d, 2H, CH$_2$), 7.5 (AA'BB', Δ=295 Hz, 4H, Ar).

Compounds IN, IV, IW, JB, JC, and JD were prepared analogously starting from the commercially available substituted 4-cyanophenols. 3-Bromocyanophenol used in the synthesis of the compound JC was prepared by bromination of 4-cyanophenol in acetic acid using bromine as described in Minoshima et. al., JP 10139770 (1998). Compound JE was prepared be reacting Compound JC with potassium cyanide in the presence of catalytic amount of Ni[(PPh$_3$)$_4$] in N-methylpyrrolidone as described in Minoshima et. al., JP 10139770 (1998).

5.6. Example 6

Compounds FF-FQ, FU, FY, HE, HF, HG-HJ, HM, JP, and JR

These compounds were obtained from the commercially available substituted benzonitriles using the Method B.

5.7. Example 7

Compounds of Formula DL

Compounds of the Formula DL ($R_4$=Bzl, Et, tert-Bu) were obtained from Compound HE using Method C (described in Section 4.4), using commercially available CbzCl, $ClCO_2Et$, and $Boc_2O$, respectively.

5.8. Example 8

Compound FR

Compound FR was synthesized by reacting a commercially available 4-aminobenzonitrile with acetic anhydride as described in *Vogel's Textbook of Practical Organic Chemistry* 5th Ed., p. 917 and then converting a resulting 4-acetylaminobenzonitrile to Compound FR following the Method B.

5.9. Example 9

Compounds FS and IU

Compounds FS and IU were synthesized by reacting 4-aminobenzonitrile with methylisocyanate or phenylisocyanate, respectively, as described in Vishnyakova et al., *Russ. Chem. Rev.*, 1985, 54, 249 and then converting the resulting urea derivative to the respective 5-Aryltetrazole Compound following Method B. 5.10. Example 10

Compound HN

Compound HN was prepared by reacting commercially available 5-aminotetrazole with cinnamoyl chloride as described in *Vogel's Textbook of Practical Organic Chemistry* 5th Ed., p. 917.

5.11. Example 11

Compounds HU and HV

Compounds HU and HV were prepared by reacting commercially available 4-cyanobenzoylsulfonyl chloride with adamantyl amine and cyclohexylamine, respectively, and then converting a resulting amide to a tetrazole as described in Example 5.1. above. 5.12. Example 12

Compound IT

Compound IT was prepared by benzoylation of 4-aminobenzonitrile as described in *Vogel's Textbook of Practical Organic Chemistry* 5th Ed., p. 917 and then converting a resulting N-benzoyl-4-cyanoaniline to Compound IT following the Method B (Sect. 4.4).

5.13. Example 13

Xanthine Oxidase Inhibitory Activity of Illustrative 5-Aryl Tetrazole Compounds A typical assay showing of xanthine oxidase inhibitory activity of illustrative 5-Aryltetrazole Compounds involved the use of a 96 well plate setup. Analysis of the sample utilized a Spectrophotometer with a SoftMax Pro Program set at a kinetic reading at a wavelength of 295 nm with a runtime of 10 minutes taking a reading at 12 second intervals. Before the first reading the sample was mixed using an automixer for five seconds and between readings the sample was mixed for three seconds.

Sample Preparation: Approximately 1–2 mg of a 5-Aryltetrazole Compound was placed in a 5 mL vial and dissolved in about 1 mL of DMSO resulting in a 2.5 mM solution.

Well Plate Preparation: Four to eight wells were used for each 5-Aryltetrazole Compound. In each well was added 200 mL of Phosphate-buffered saline (50 mM), 20 mL of xanthine (0.5 mg/mL in water), 10 mL of the 2.5 mM solution of 5-Aryltetrazole Compound (prepared as described above), and 20 mL of xanthine oxidase (1/100×40 mL PBS). The xanthine oxidase was kept on ice and was added immediately before the plate was run on the spectrophotometer. A control well was also prepared using only DMSO.

The following table shows concentrations of illustrative 5-Aryltetrazole Compounds providing xanthine-oxidase inhibition. Without being limited by theory, compounds that inhibit xanthine oxidase are useful for treating or preventing an inflammation disease, a reperfusion disease, or hyperuricemia.

| PERCENT XANTHINE OXIDASE INHIBITION | | | | | | | |
|---|---|---|---|---|---|---|---|
| | 5-Aryltetrazole Compound Concentration (μM) | | | | | | |
| Compound | 100 | 10 | 1 | 0.1 | 0.05 | 0.03 | 0.01 |
| FF | 10 | NT | NT | NT | NT | NT | NT |
| FG | 34 | NT | NT | NT | NT | NT | NT |
| FH | 69 | 27 | NT | NT | NT | NT | NT |
| FI | 67 | 21 | NT | NT | NT | NT | NT |
| FJ | 7 | 5 | NT | NT | NT | NT | NT |
| FK | 71 | 30 | NT | NT | NT | NT | NT |
| FL | 55 | 14 | NT | NT | NT | NT | NT |
| FM | 78 | 19 | NT | NT | NT | NT | NT |
| FN | 32 | 3 | NT | NT | NT | NT | NT |
| FO | 30 | 3 | NT | NT | NT | NT | NT |
| FP | 21 | 3 | NT | NT | NT | NT | NT |
| FQ | 99 | 81 | 34 | NT | NT | NT | NT |
| FR | 40 | NT | NT | NT | NT | NT | NT |
| FS | 10 | NT | NT | NT | NT | NT | NT |
| FT | 67 | 70 | 15 | NT | NT | NT | NT |
| FU | 92 | 54 | 9 | NT | NT | NT | NT |
| FV | 100 | 92 | 64 | NT | NT | NT | NT |
| FW | 100 | 82 | 39 | NT | NT | NT | NT |
| FX | 95 | 95 | 73 | NT | NT | NT | NT |
| FY | 91 | 56 | 11 | NT | NT | NT | NT |
| FZ | 100 | 97 | 88 | NT | NT | NT | NT |
| GA | 100 | 100 | 78 | NT | NT | NT | NT |
| GB | 100 | 97 | 82 | NT | NT | NT | NT |
| GC | NT | NT | 100 | 97 | 52 | NT | NT |
| GD | 100 | 82 | 79 | NT | NT | NT | NT |
| GE | NT | NT | 100 | 100 | 59 | NT | NT |
| GF | 97 | 79 | 28 | NT | NT | NT | NT |
| GG | 89 | 97 | 90 | NT | NT | NT | NT |
| GH | NT | NT | 100 | 91 | NT | 65 | NT |
| GI | NT | NT | 100 | 95 | NT | 75 | NT |
| GJ | NT | NT | 99 | 59 | NT | NT | 12 |
| GK | NT | NT | 46 | 12 | NT | NT | 3 |
| GL | NT | NT | 4 | NT | NT | NT | NT |
| GM | NT | NT | 76 | 28 | NT | NT | 8 |
| GN | NT | NT | 9 | NT | NT | NT | NT |
| GO | NT | NT | 82 | 18 | NT | NT | 6 |
| GP | NT | NT | 92 | 65 | NT | NT | 9 |
| GQ | NT | NT | 78 | 35 | NT | NT | 0 |
| GR | NT | NT | 48 | 8 | NT | NT | 0 |
| GS | NT | NT | 95 | 68 | NT | NT | 13 |
| GT | NT | NT | 94 | 53 | NT | NT | 8 |
| GU | NT | NT | 94 | 69 | NT | NT | 17 |
| GV | NT | NT | 95 | 73 | NT | NT | 14 |
| GW | NT | NT | 39 | 9 | NT | NT | 5 |

PERCENT XANTHINE OXIDASE INHIBITION

| Compound | \multicolumn{7}{c}{5-Aryltetrazole Compound Concentration (μM)} | | | | | | |
|---|---|---|---|---|---|---|---|
| | 100 | 10 | 1 | 0.1 | 0.05 | 0.03 | 0.01 |
| GX | NT | NT | 100 | 84 | NT | NT | 19 |
| GY | NT | NT | 76 | 11 | NT | NT | 19 |
| GZ | NT | NT | 8 | NT | NT | NT | NT |
| HA | NT | NT | 61 | 10 | NT | NT | NT |
| HB | NT | NT | 25 | NT | NT | NT | NT |
| HC | NT | NT | 25 | NT | NT | NT | NT |
| HD | 60 | NT | NT | NT | NT | NT | NT |
| HE | 33 | NT | NT | NT | NT | NT | NT |
| HF | 80 | NT | NT | NT | NT | NT | NT |
| HG | 22 | NT | NT | NT | NT | NT | NT |
| HH | 48 | NT | NT | NT | NT | NT | NT |
| HI | 70 | 24 | 14 | NT | NT | NT | NT |
| HJ | 2 | NT | NT | NT | NT | NT | NT |
| HK | 43 | NT | NT | NT | NT | NT | NT |
| HL | 0 | NT | NT | NT | NT | NT | NT |
| HM | 27 | NT | NT | NT | NT | NT | NT |
| HN | 42 | 13 | 10 | NT | NT | NT | NT |
| HO | NT | NT | 98 | 95 | 46 | NT | NT |
| HP | NT | NT | 100 | 91 | 41 | NT | NT |
| HQ | NT | NT | 95 | 97 | 53 | NT | NT |
| HR | NT | NT | 95 | 95 | 34 | NT | NT |
| HS | NT | NT | 55 | 16 | NT | 8 | NT |
| HT | NT | NT | 62 | 23 | NT | 15 | NT |
| HU | NT | NT | 0 | NT | NT | NT | NT |
| HV | NT | NT | 0 | NT | NT | NT | NT |
| HW | NT | NT | 89 | 62 | NT | 32 | NT |
| HX | NT | NT | 92 | 59 | NT | 37 | NT |
| HY | NT | NT | 86 | 45 | NT | 20 | NT |
| HZ | NT | NT | 88 | 41 | NT | 20 | NT |
| IA | NT | NT | 90 | 54 | NT | 31 | NT |
| IB | NT | NT | 94 | 64 | NT | 38 | NT |
| IC | NT | NT | 100 | 81 | NT | 60 | NT |
| ID | NT | NT | 72 | 37 | NT | 13 | NT |
| IE | NT | NT | 87 | 38 | NT | 22 | NT |
| IF | NT | NT | 16 | NT | NT | NT | NT |
| IG | NT | NT | 93 | 59 | NT | 33 | NT |
| IH | NT | NT | 95 | 63 | NT | 33 | NT |
| II | NT | NT | 90 | 45 | NT | 20 | NT |
| IJ | NT | NT | 93 | 58 | NT | 27 | NT |
| IK | NT | NT | 55 | 17 | NT | 9 | NT |
| IL | NT | NT | 86 | 46 | NT | 21 | NT |
| IM | NT | NT | 0 | NT | NT | NT | NT |
| IN | NT | NT | 68 | 21 | NT | NT | NT |
| IO | NT | NT | 0 | NT | NT | NT | NT |
| IP | NT | NT | 92 | 52 | NT | 28 | NT |
| IQ | NT | NT | 64 | 33 | NT | 36 | NT |
| IR | NT | NT | 88 | 47 | NT | 28 | NT |
| IS | NT | NT | 97 | 68 | NT | 44 | NT |
| IT | NT | NT | 56 | 15 | NT | 7 | NT |
| IU | NT | NT | 42 | 9 | NT | 3 | NT |
| IV | NT | NT | 35 | 10 | NT | NT | NT |
| IW | NT | NT | 22 | 9 | NT | NT | NT |
| IX | NT | NT | 98 | 74 | NT | 46 | NT |
| IY | NT | NT | 86 | 47 | NT | 26 | NT |
| IZ | NT | NT | 89 | 52 | NT | 23 | NT |
| JA | NT | NT | NT | 0 | NT | NT | NT |
| JB | NT | NT | 32 | 15 | NT | NT | NT |
| JC | NT | NT | 31 | 6 | NT | NT | NT |
| JD | NT | NT | 28 | 0 | NT | NT | NT |
| JE | NT | NT | 82 | 32 | NT | 12 | NT |
| JF | NT | NT | 34 | 6 | NT | NT | NT |
| JG | NT | NT | 93 | 61 | NT | 33 | NT |
| JH | NT | NT | 86 | 41 | NT | 23 | NT |
| JI | NT | NT | 79 | 30 | NT | 19 | NT |
| JJ | NT | NT | 0 | NT | NT | NT | NT |
| JK | NT | NT | 0 | NT | NT | NT | NT |
| JL | NT | NT | 95 | 68 | NT | 34 | NT |
| JM | NT | NT | 89 | 38 | NT | 16 | NT |
| JN | NT | NT | 88 | 41 | NT | 20 | NT |
| JO | NT | NT | 83 | 36 | NT | 18 | NT |
| JP | NT | NT | 98 | 74 | NT | 46 | NT |
| JQ | NT | NT | 100 | 89 | NT | NT | 18 |
| JR | 85 | 56 | 14 | NT | NT | NT | NT |

The term "NT" means that the compound was not tested at the indicated concentration.

The above example demonstrates that Compounds FF–HK, HM–HT, HW–IL, IN, IP–IZ, JB–JI, and JL–JR, illustrative 5-Aryltetrazole Compounds, inhibit xanthine oxidase activity and, accordingly are useful for treating or preventing an inflammation disease, a reperfusion disease, or hyperuricemia. In addition, Applicants believe that Compounds HL, HU, HV, IM, IO, JA, JJ, and JK, illustrative 5-Aryltetrazole Compounds, are useful for treating or preventing an inflammation disease, a reperfusion disease, or hyperuricemia.

5.14. Example 14

Toxic Liver Injury Model

Illustrative 5-Aryltetrazole Compounds exert hepatoprotective effects in a thioacetamide model of hepatic failure. The table below shows the efficacy of various illustrative 5-Aryltetrazole Compounds for their hepatoprotective activity in mice. Illustrated are percent inhibition of the increased serum AST levels resulting from an intraperitoneal injection of thioacetamide (400 mg/kg) following a single oral dose (3 mL/kg or 10 mL/kg) of various doses of 5-Aryltetrazole Compounds. Results are expressed as percent inhibtion, mean ±SEM (n=7–10). Studies were conducted as described in *Biochim. Biophys. Acta.* 1536(1):21–30 (2001).

TOXIC LIVER INJURY MODEL

| | Percent Inhibition of Serum AST Levels | |
|---|---|---|
| Compound | 3 mg/kg | 10 mg/kg |
| IC | 3 ± 8 | 20 ± 5 |
| IG | 25 ± 4 | 46 ± 8 |
| IP | 23 ± 8 | 41 ± 8 |
| IS | NT | 33 ± 5 |
| JM | 12 ± 7 | 31 ± 7 |
| JN | 11 ± 7 | 31 ± 7 |
| JO | 24 ± 9 | 36 ± 12 |
| IX | NT | 31 ± 1 |

Accordingly, the above example demonstrates that Compounds IC, IG, IP, IS, JM–JO, and IX, illustrative 5-Aryltetrazole Compounds, inhibit serum AST levels and, accordingly, are useful for treating or preventing organ failure.

5.15. Example 15

Collagen-Induced Arthritis

An illustrative 5-Aryltetrazole Compound exerts protective effects in a model of collagen-induced arthritis in mice. Results are expressed as incidence and severity over time.

Studies were conducted as described in *Inflamm. Res.* 50(11):561–569 (2001). The results illustrate that the administration of Compound JO, an illustrative 5-Aryltetrazole Compound, reduced incidence of collagen-induced arthritis in mice. Specifically, after 33 days 100% of the untreated mice exhibited arthritis; however, mice that were administered Compound JO showed a significant decrease in the incidence of collagen-induced arthritis.

|  | Time (days) | | | | |
| --- | --- | --- | --- | --- | --- |
|  | 25 | 27 | 29 | 31 | 33 |
| % Incidence Vehicle | 35 | 45 | 55 | 90 | 100 |
| Compound JO | 20 | 35 | 45 | 75 | 85 |
| Mean Severity Vehicle | 0 | 0 | 8 | 10 | 12 |
| Compound JO | 0 | 0 | 3 | 8 | 8 |

The above example demonstrates that Compound JO, an illustrative 5-Aryltetrazole Compound, inhibits collagen-induced arthritis and accordingly, is useful for treating or preventing arthritis.

5.16. Example 16

Reperfusion Injury

Illustrative 5-Aryltetrazole Compounds exert protective effects in various models of organ ischemia and reperfusion. For example, intraperitoneal administration of illustrative 5-Aryltetrazole Compounds retards the progression of gut ischemia reperfusion-induced hyperpermeability and mortality in mice. Results are expressed as % decrease in gut hyperpermeability and as mortality as observed after 6 hours and 2 days of reperfusion. Studies were conducted as described in *Shock*, 14(2):134–141 (2000). There was a notable dose-dependent effect on gut hyperpermeability and there was an improvement in survival rate, as tested at the highest dose of both levels.

|  |  | Dose | | | |
| --- | --- | --- | --- | --- | --- |
|  |  | 3 mg/kg | 10 mg/kg | 30 mg/kg | 30 mg/kg |
| Compound | Control | IG | IG | IG | JO |
| Gut Permeability | 100% | 73% | 69% | 47% | 39% |

|  |  | Dose | |
| --- | --- | --- | --- |
|  |  | 30 mg/kg | 30 mg/kg |
| Compound | Control | IG | JO |
| Survival % (6 h) | 60 | 87 | 87 |
| Survival % (2days) | 0 | 20 | 13 |

The above example demonstrates that Compound IG and JO, illustrative 5-Aryltetrazole Compounds, are useful for treating or preventing a reperfusion disease in an animal.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosures of which have been incorporated herein in their entirety.

What is claimed is:

1. A method for treating an inflammation disease in an animal, comprising administering to an animal in need thereof an effective amount of a compound having the formula:

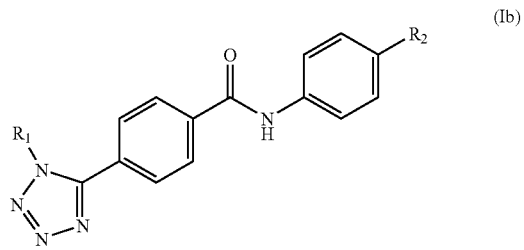

(Ib)

or a pharmaceutically acceptable salt or hydrate thereof, wherein:

$R_1$ is —H, —$CO_2R_4$, —$C(O)R_5$, or —$C(O)N(R_5)(R_5)$;
$R_2$ is —($C_1$–$C_{10}$)alkyl or —$O(C_1$–$C_{10}$)alkyl;
$R_4$ is —($C_5$)heteroaryl, —($C_6$)heteroaryl, phenyl, naphthyl, or benzyl; and
each occurrence of $R_5$ is independently —H, —$CF_3$, —($C_1$–$C_{10}$)alkyl, -benzyl, —($C_2$–$C_{10}$)alkenyl, —($C_2$–$C_{10}$)alkynyl, —($C_3$–$C_{10}$)cycloalkyl, —($C_8$–$C_{14}$)bicycloalkyl, or —($C_3$–$C_{10}$)heterocycle, wherein the inflammation is related to or associated with arthritis, psoriasis, gingivitis, colitis, uveitis, diabetes, adult respiratory distress syndrome, autoimmune disease, lupus erythematosus, ileitis, ulcerative colitis, Crohn's disease, asthma, periodontitis, ophthalmitis, endophthalmitis, nephrosis, AIDS-related neurodegeneration, stroke, neurotrauma, Alzheimer's disease, encephalomyelitis, cardiomyopathy, or transplant rejection.

2. A method for treating a reperfusion disease in an animal, comprising administering to an animal in need thereof an effective amount of a compound having the formula:

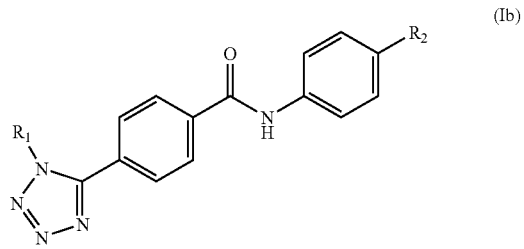

(Ib)

or a pharmaceutically acceptable salt or hydrate thereof, wherein:

$R_1$ is —H, —$CO_2R_4$, —$C(O)R_5$, or —$C(O)N(R_5)(R_5)$;
$R_2$ is —($C_1$–$C_{10}$)alkyl or —$O(C_1$–$C_{10}$)alkyl;
$R_4$ is —($C_5$)heteroaryl, —($C_6$)heteroaryl, phenyl, naphthyl, or benzyl; and
each occurrence of $R_5$ is independently —H, —$CF_3$, —($C_1$–$C_{10}$)alkyl, -benzyl, —($C_2$–$C_{10}$)alkenyl, —(C$_2$–C$_{10}$)alkynyl, —(C$_3$–C$_{10}$)cycloalkyl, —(C$_8$–C$_{14}$)bicycloalkyl, or —(C$_3$–C$_{10}$)heterocycle, wherein the reperfusion disease is related to or associated with hemorrhagic shock, sepsis, septic shock, myocardial infarction, stroke, cell or solid-organ transplantation, or cardiopulmonary bypass surgery.

3. A method for treating hyperuricemia in an animal, comprising administering to an animal in need thereof an effective amount of a having the formula:

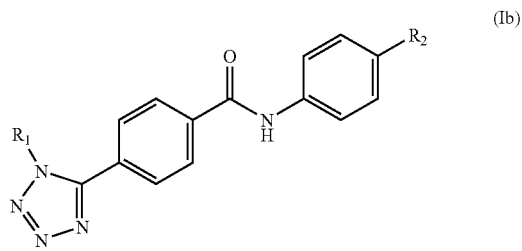
(Ib)

or a pharmaceutically acceptable salt or hydrate thereof, wherein:
R$_1$ is —H, —CO$_2$R$_4$, —C(O)R$_5$, or —C(O)N(R$_5$)(R$_5$);
R$_2$ is —(C$_1$–C$_{10}$)alkyl or —O(C$_1$–C$_{10}$)alkyl;
R$_4$ is —(C$_5$)heteroaryl, —(C$_6$)heteroaryl, phenyl, naphthyl, or benzyl; and
each occurrence of R$_5$ is independently —H, —CF$_3$, —(C$_1$–C$_{10}$)alkyl, -benzyl, —(C$_2$–C$_{10}$)alkenyl, —(C$_2$–C$_{10}$)alkynyl, —(C$_3$–C$_{10}$)cycloalkyl, —(C$_8$–C$_{14}$)bicycloalkyl, or —(C$_3$–C$_{10}$)heterocycle.

4. The method of claim 3, wherein the hyperuricemia is gout.

5. A method for treating tumor-lysis syndrome in an animal, comprising administering to an animal in need thereof an effective amount of a having the formula:

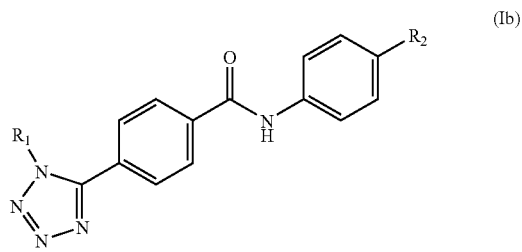
(Ib)

or a pharmaceutically acceptable salt or hydrate thereof, wherein:
R$_1$ is —H, —CO$_2$R$_4$, —C(O)R$_5$, or —C(O)N(R$_5$)(R$_5$);
R$_2$ is —(C$_1$–C$_{10}$)alkyl or —O(C$_1$–C$_{10}$)alkyl;
R$_4$ is —(C$_5$)heteroaryl, —(C$_6$)heteroaryl, phenyl, naphthyl, or benzyl; and
each occurrence of R$_5$ is independently —H, —CF$_3$, —(C$_1$–C$_{10}$)alkyl, -benzyl, —(C$_2$–C$_{10}$)alkenyl, —(C$_2$–C$_{10}$)alkynyl, —(C$_3$–C$_{10}$)cycloalkyl, —(C$_8$–C$_{14}$)bicycloalkyl, or —(C$_3$–C$_{10}$)heterocycle.

6. A method for treating an inflammatory bowel disorder in an animal, comprising administering to an animal in need thereof an effective amount of a compound having the formula:

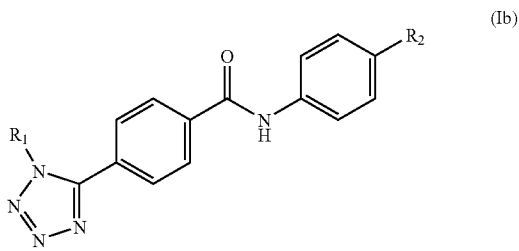
(Ib)

or a pharmaceutically acceptable salt or hydrate thereof, wherein:
R$_1$ is —H, —CO$_2$R$_4$, —C(O)R$_5$, or —C(O)N(R$_5$)(R$_5$);
R$_2$ is —(C$_1$–C$_{10}$)alkyl or —O(C$_1$–C$_{10}$)alkyl;
R$_4$ is —(C$_5$)heteroaryl, —(C$_6$)heteroaryl, phenyl, naphthyl, or benzyl; and
each occurrence of R$_5$ is independently —H, —CF$_3$, —(C$_1$–C$_{10}$)alkyl, -benzyl, —(C$_2$–C$_{10}$)alkenyl, —(C$_2$–C$_{10}$)alkynyl, —(C$_3$–C$_{10}$)cycloalkyl, —(C$_8$–C$_{14}$)bicycloalkyl, or —(C$_3$–C$_{10}$)heterocycle, wherein the inflammatory bowel disorder is ileitis, colitis, Crohn's disease or pouchitis.

7. The method of claim 1 wherein the compound of formula (Ib) is:

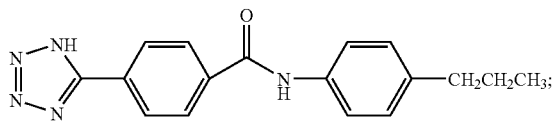

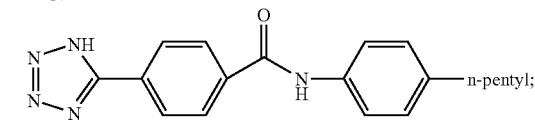

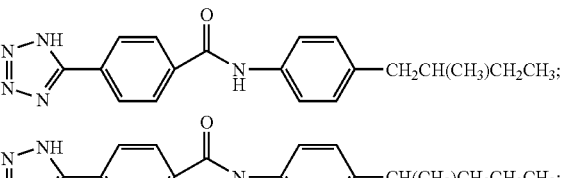

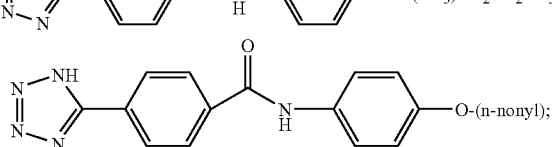

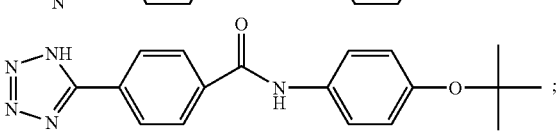

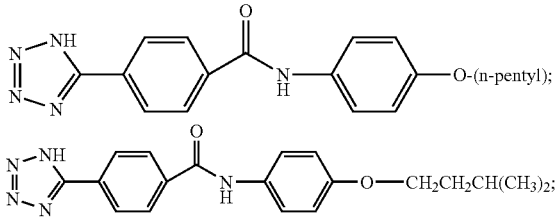

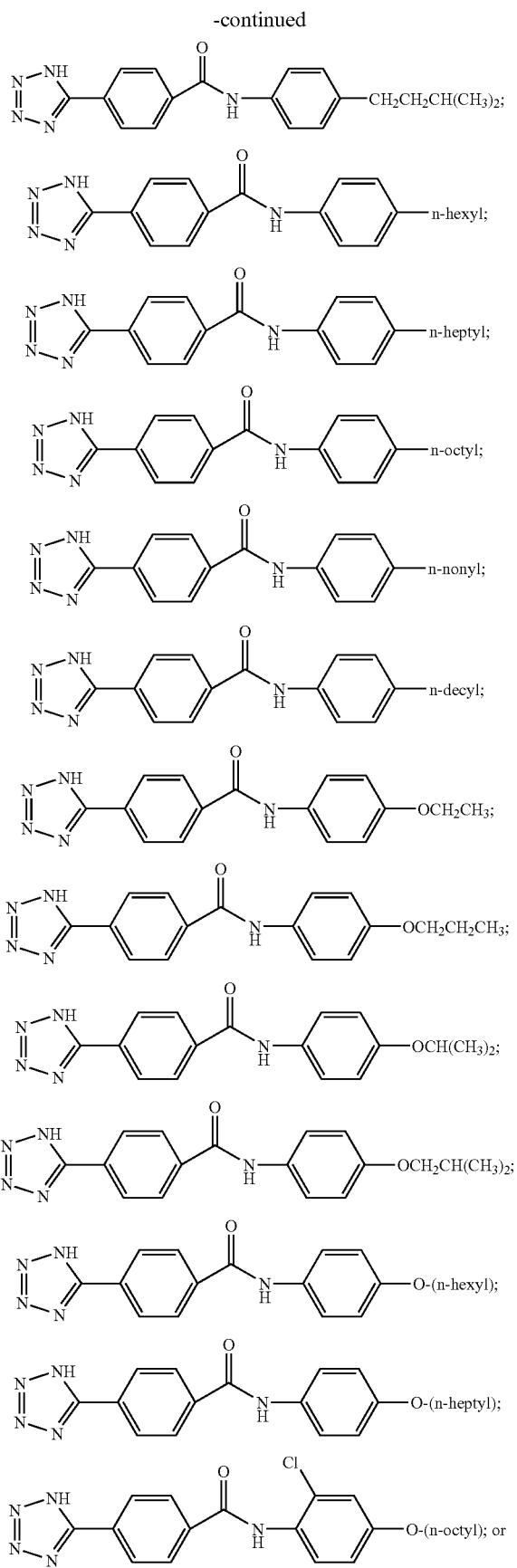
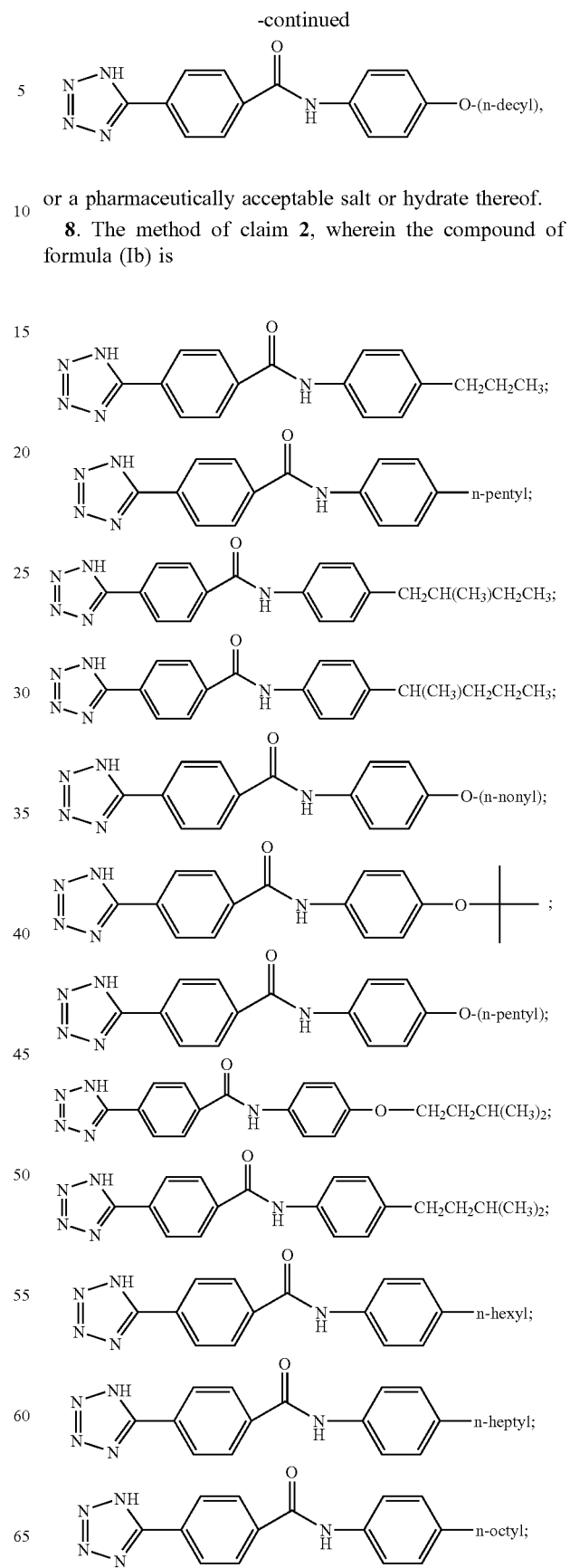
or a pharmaceutically acceptable salt or hydrate thereof.
8. The method of claim 2, wherein the compound of formula (Ib) is

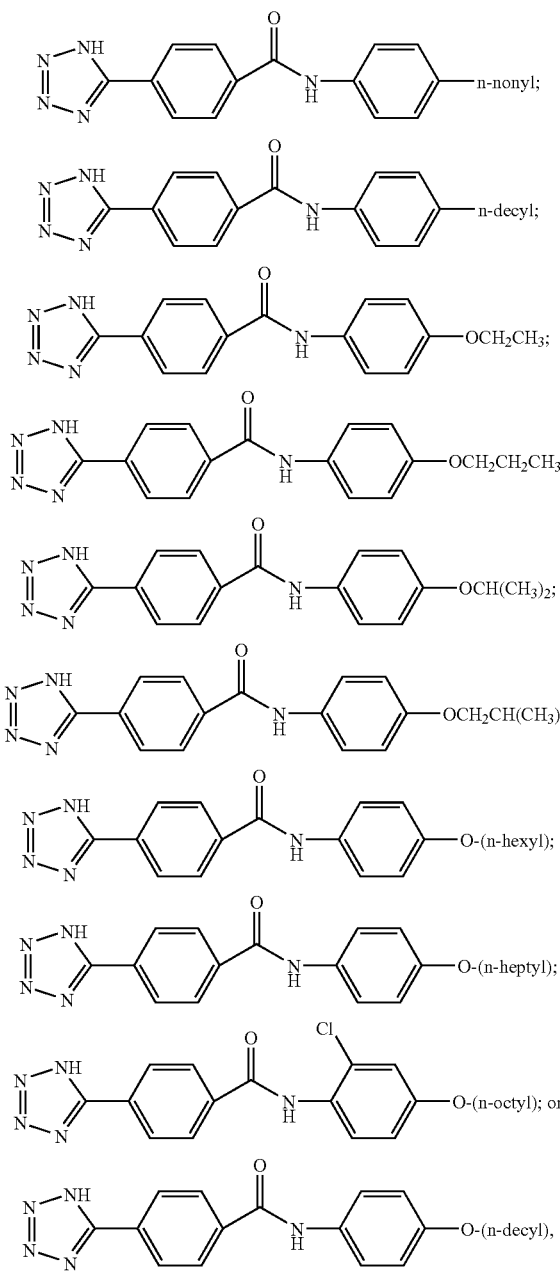
or a pharmaceutically acceptable salt or hydrate thereof.
9. The method of claim 3, wherein the compound of formula (Ib) is
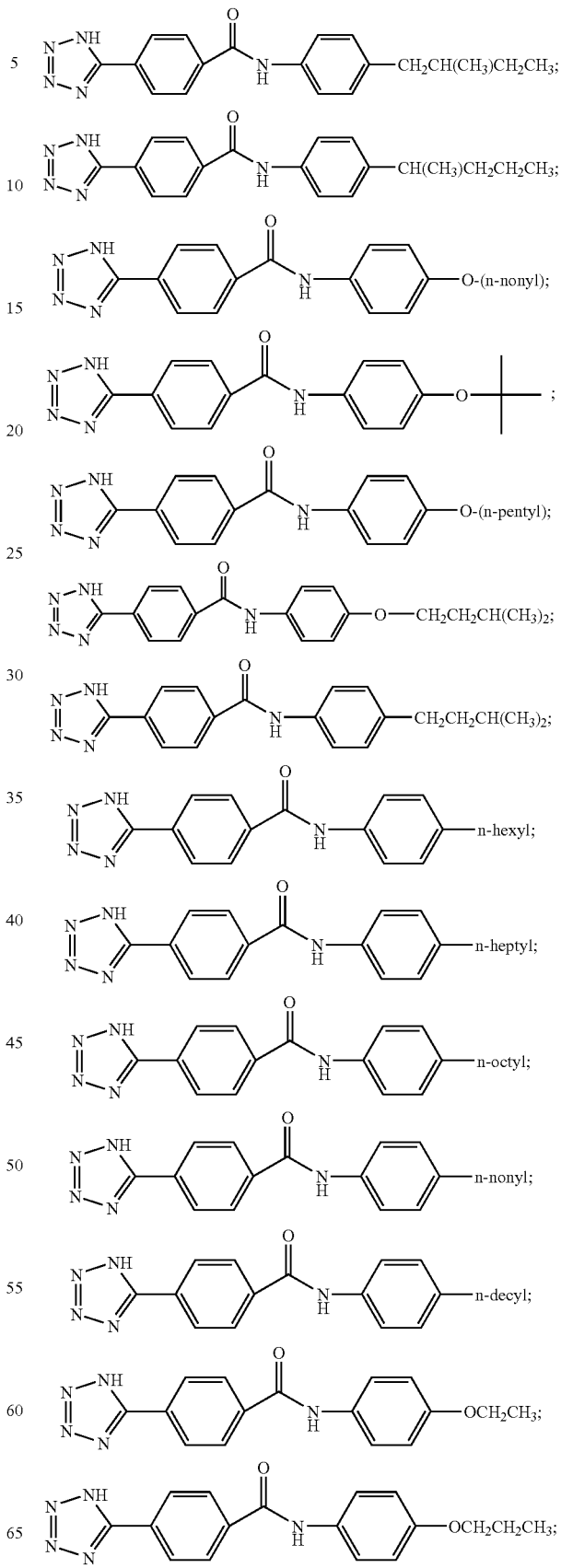

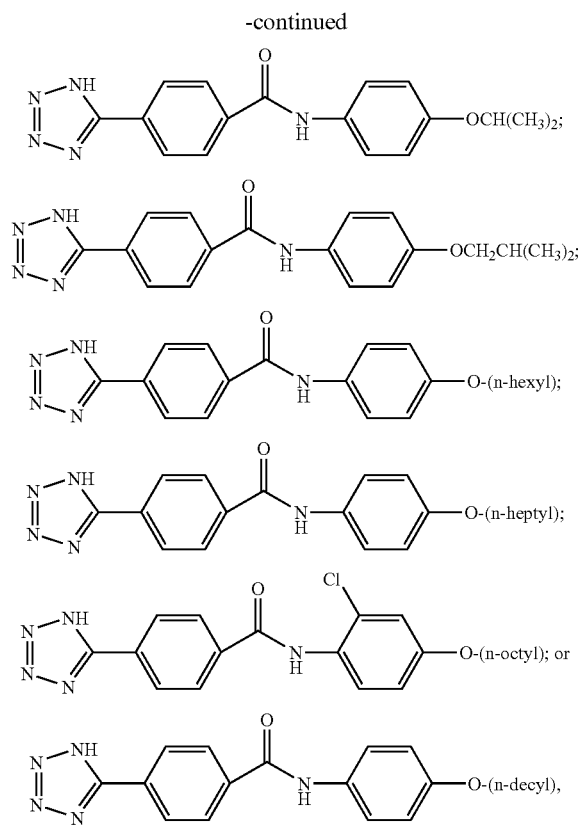
or a pharmaceutically acceptable salt or hydrate thereof.
10. The method of claim 5, wherein the compound of formula (Ib) is
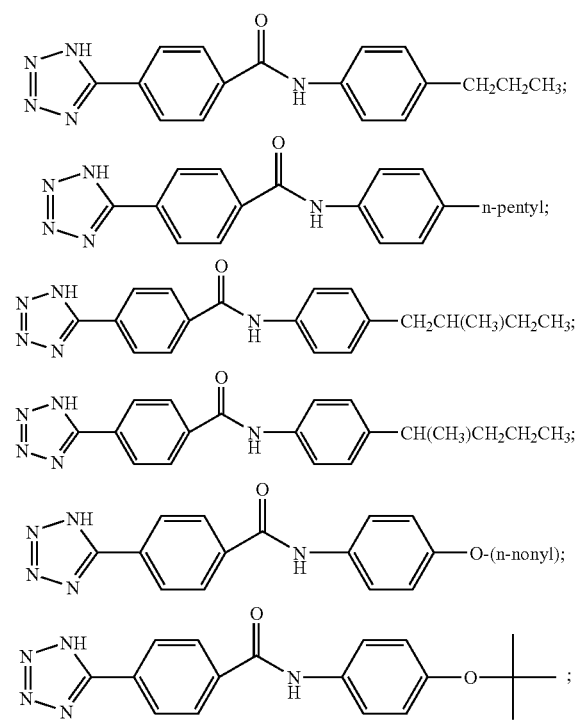
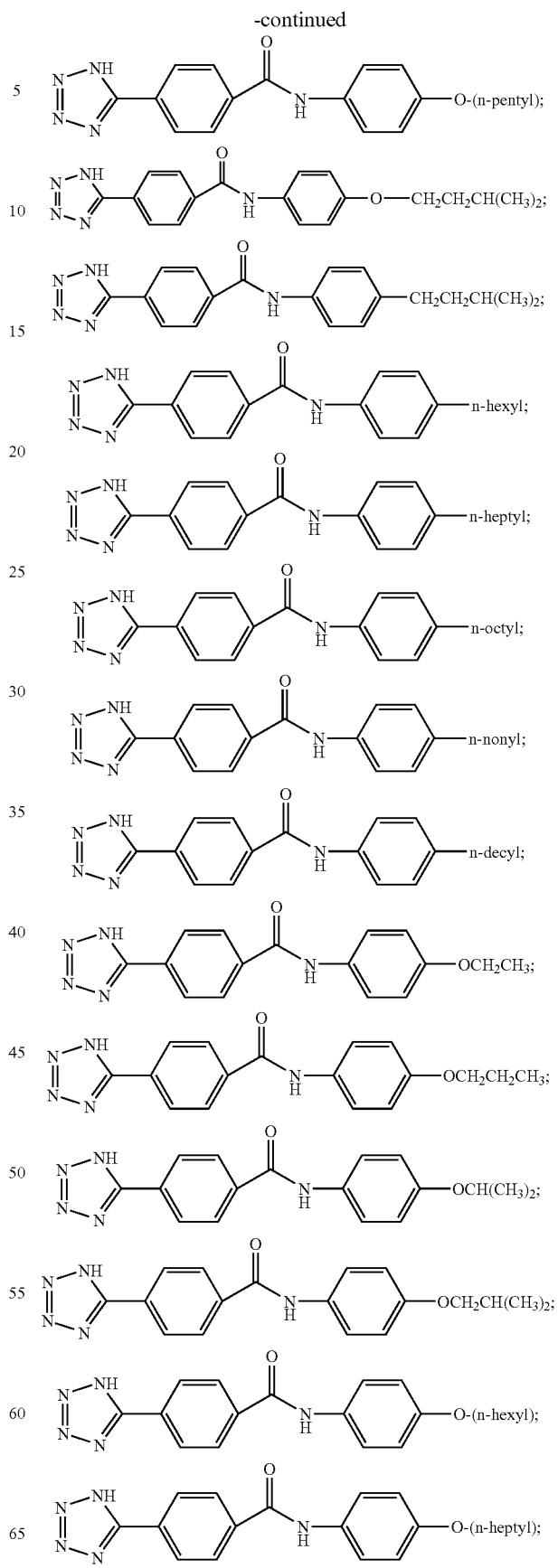

-continued

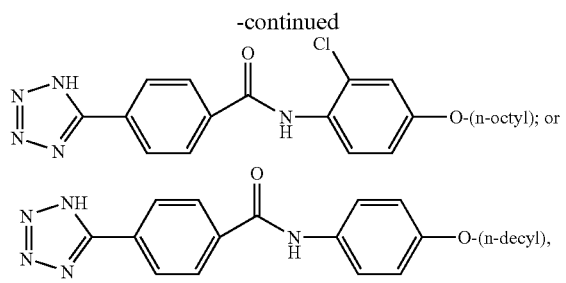

or a pharmaceutically acceptable salt or hydrate thereof.

11. The method of claim 6, wherein the compound of formula (Ib) is

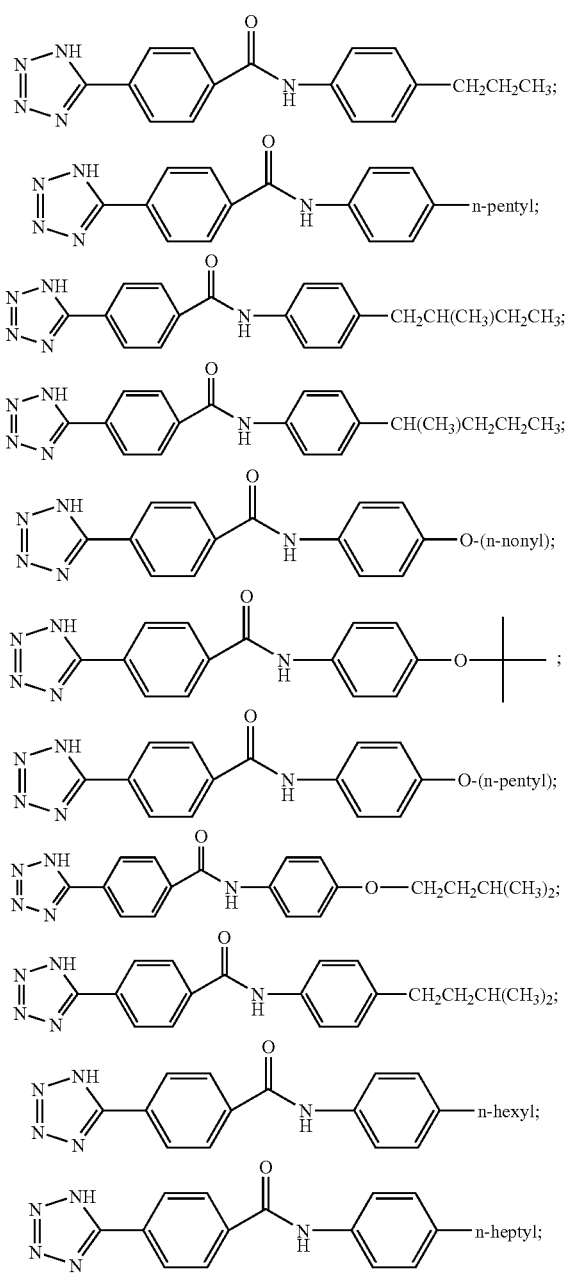

or a pharmaceutically acceptable salt or hydrate thereof.

12. The method of claim 6, wherein the ileitis is regional ileitis.

13. The method of claim 6, wherein the colitis is ulcerative colitis, enterocolitis, or collagenous microscopic colitis.

* * * * *